United States Patent [19]

Ahern

[11] Patent Number: 5,470,724
[45] Date of Patent: Nov. 28, 1995

[54] BOOMERANG DNA AMPLIFICATION

[75] Inventor: Kevin G. Ahern, Corvallis, Oreg.

[73] Assignee: State of Oregon Acting by and through the Oregon State Board of Higher Education on behalf of Oregon State University, Eugene, Oreg.

[21] Appl. No.: 184,941

[22] Filed: Jan. 19, 1994

Related U.S. Application Data

[63] Continuation of Ser. No. 841,320, Feb. 20, 1992, abandoned.
[51] Int. Cl.[6] .................................................... C12P 19/34
[52] U.S. Cl. .................... 435/91.2; 536/24.3; 536/24.2
[58] Field of Search ....................... 435/91.2; 536/24.3, 536/24.2

[56] References Cited

U.S. PATENT DOCUMENTS

| | | | |
|---|---|---|---|
| 4,965,188 | 10/1990 | Mullis et al. | 435/6 |
| 4,994,370 | 2/1991 | Silver et al. | 435/6 |

OTHER PUBLICATIONS

Kalisch et al., "Covalently Linked Sequencing Primer Linkers (Splinkers) for Sequence Analysis of Restriction Fragments, (Recombinant DNA; Hairpin Ligation; Synthetic Oligodeoxynucleotides; Dideoxynucleotides)," *Gene* 44:263–270 (1986).
Murray, "Improved Double–Stranded DNA Sequencing Using the Linear Polymerase Chain Reaction," *Nucl. Acids Res.* 17:8889 (1989).
Dulau et al., "Directed Mutagenesis Using PCR," *Nucl. Acids Res.* 17:2873 (1989).
Mullis, "The Polymerase Chain Reaction: Why It Works," in Erlich et al. (eds.) *Current Communications in Molecular Biology: Polymerase Chain Reaction*, pp. 237–243, Cold Spring Harbor Laboratory (1989).
Parker et al., "Targeted Gene Walking Polymerase Chain Reaction," *Nucl. Acids Res.* 19:3055–3060 (1991).
Earp et al., "Amplification of Genomic Sequences Flanking Transposable Elements in Host and Heterologous Plants: A Tool for Transposon Tagging and Genome Characterization," *Nucl. Acids Res.* 18:3271–3279 (1990).
Wong, et al., "Branch Capture Reactions: Displacers Derived from Asymmetric PCR," *Nucl. Acids Res.* 19:2251–2259 (1991).
Aslanidis et al., "Ligation–Independent Cloning of PCR Products (LIC–PCR)," *Nucl. Acids Res.* 18:6069–6074 (1990).
Jones et al., "Sequence Specific Generation of a DNA Panhandle Permits PCR Amplification of Unknown Flanking DNA," *Nucl. Acids Res.* 20:595–600 (1992).
Lo et al., "Direct Haplotype Determination by Double ARMS: Specificity, Sensitivity and Genetic Applications," *Nucl. Acids Res.* 19:3561–3567 (1991).

*Primary Examiner*—Margaret Parr
*Assistant Examiner*—Scott William Houtteman
*Attorney, Agent, or Firm*—Klarquist Sparkman Campbell Leigh & Whinston

[57] ABSTRACT

Methods for amplifying DNA sequences of interest are disclosed. The methods can be performed using only one primer and are also useful in cloning protocols and for sequencing large DNAs. The methods comprise cleaving a sample DNA using an agent, such as a restriction endonuclease, that produces discrete DNA fragments; ligating the fragments to "adapter" polynucleotides having a ligatable end and first and second self-complementary sequences separated by a spacer sequence, thereby forming ligated duplexes; denaturing the ligated duplexes to form templates; annealing molecules of an oligonucleotide primer to the templates, the primers being homologous to a primer target site associated with the sequence of interest; extending the primers using a DNA polymerizing agent to form duplex products; and denaturing the duplex products. Subsequent multiple cycles of annealing primers, extending the primers, and denaturing duplex products are usually performed so as to achieve the desired degree of amplification. Sequencing of large DNAs is performed using multiple rounds of DNA amplification, each round employing a primer homologous with a primer target site in the sequence of interest previously amplified. Cloning is facilitated by including a replication origin and selectable marker in the adapters.

44 Claims, 14 Drawing Sheets

OTHER PUBLICATIONS

Lechner et al., "The Structure of Replicating Adenovirus 2 DNA Molecules," *Cell* 12:1007–1020 (1977).

Gyllensten et al., "Generation of Single–Stranded DNA by the Polymerase Chain Reaction and its Application to Direct Sequencing of the *HLA–DQA* Locus," *Proc. Natl. Acad. Sci. USA* 85:7652–7656 (1988).

Frohman, et al., "Rapid Production of Full–Length cDNAs from Rare Transcripts: Amplification Using a Single Gene–Specific Oligonucleotide Primer," *Proc. Natl. Acad. Sci. USA* 85:8998–9002 (1988).

Jayaraman, et al., "Polymerase Chain Reaction–Mediated Gene Synthesis: Synthesis of a Gene Coding for Isozyme c of Horseradish Peroxidase," *Proc. Natl. Acad. Sci. USA* 88:4084–4088 (1991).

Nickerson, et al., "Automated DNA Diagnostics Using an ELISA–Based Oligonucleotide Ligation Assay," *Proc. Natl. Acad. Sci USA* 87:8923–8927 (1990).

Mueller et al., "In Vivo Footprinting of a Muscle Specific Enhancer by Ligation Mediated PCR," *Science* 246:780–786 (1989).

Chao et al., "Sequence Conservation and Divergence of Hepatitis $\delta$ Virus RNA," *Virology* 178:384–392 (1990).

Cariello, et al., "Deletion Mutagenesis During Polymerase Chain Reaction: Dependence on DNA Polymerase," *Gene* 99:105–108 (1991).

Shuldiner et al., "RNA Template–Specific PCR: An Improved Method that Dramatically Reduces False Positives in RT–PCR," *BioTechniques* 11:760–763 (1991).

Buck et al., "A General Method for Quantitative PCR Analysis of mRNA Levels for Members of Gene Families: Application to $GABA_A$ Receptor Subunits," *BioTechniques* 11:636–639 (1991).

Roux et al., "A Strategy for Single Site PCR Amplification of dsDNA: Priming Digested Cloned or Genomic DNA from an Anchor–Modified Restriction Site and a Short Internal Sequence," *BioTechniques* 8:48–57 (1990).

Horton et al., "Gene Splicing by Overlap Extension: Tailor–Made Genes Using the Polymerase Chain Reaction," *BioTechniques* 8:528–535 (1990).

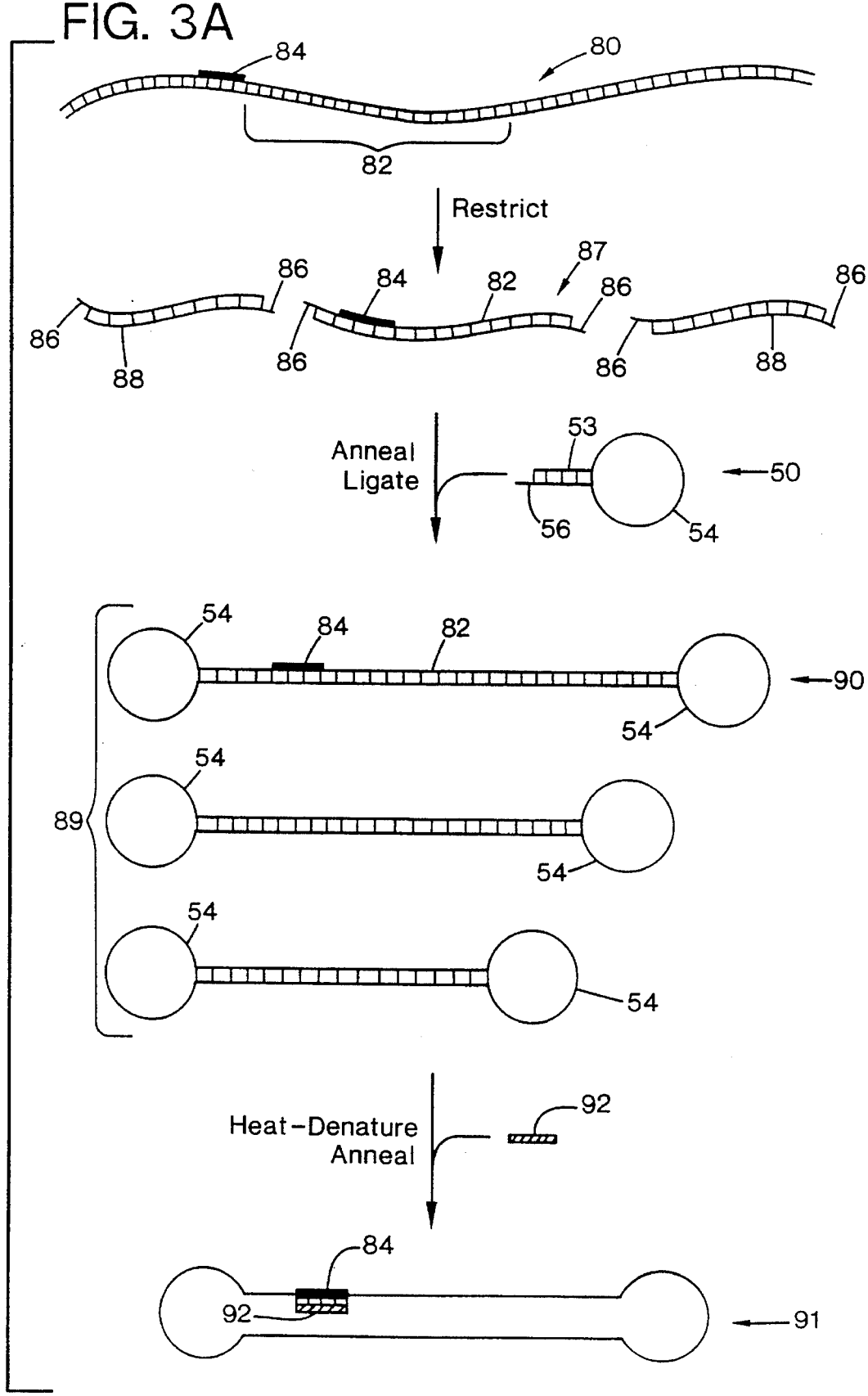

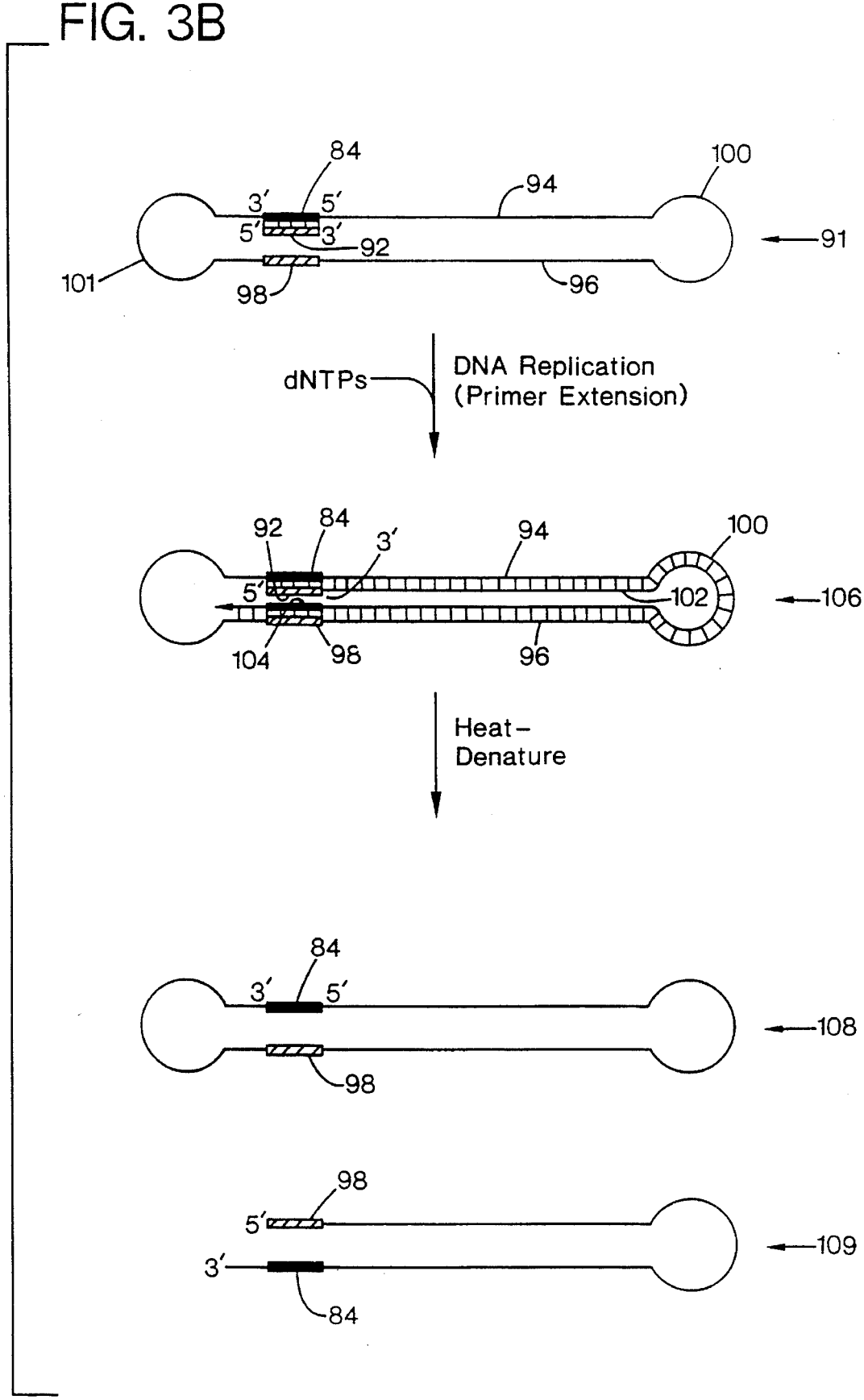

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 77 BASE PAIRS
        ( B ) TYPE: Nucleic Acid
        ( C ) STRANDEDNESS: Double- Stranded
        ( D ) TOPOLOGY: Linear ( i i ) MOLECULE TYPE: Other nucleic acid
        ( A ) DESCRIPTION: Plasmid polylinker ( i i i ) HYPOTHETICAL: No ( i v ) ANTI-SENSE: No ( v i ) ORIGINAL SOURCE:
        ( A ) ORGANISM: Escherichia coli ( v i i ) IMMEDIATE SOURCE:
        ( A ) LIBRARY: None
        ( B ) CLONE: BDA I, constructed from pUC19

( v i i i ) POSITION IN GENOME:
        ( C ) UNITS: Nucleotides 396 to 451 of BDA I ( i x ) FEATURE:
        ( A ) NAME/KEY: Polylinker OF pUC19

( x i ) SEQUENCE DESCRIPTION: SEQ ID NO:1:

```
AGTGAATTCG  AGCTCGGTAC  CCGGGGATCC  TCTAGAGTCG  ACCTGCAGGC  ATGCAAGCTT    60
```

GGCGTAATCA TGGTCAT 77

( 2 ) INFORMATION FOR SEQ ID NO:2:

( i ) SEQUENCE CHARACTERISTICS:
        ( A ) LENGTH: 121 Bases
        ( B ) TYPE: Nucleic Acid
        ( C ) STRANDEDNESS: Both Single- Stranded and Double-Stranded Regions
        ( D ) TOPOLOGY: Linear ( i i ) MOLECULE TYPE: Other nucleic acid
        ( A ) DESCRIPTION: BDA Adapter ( i i i ) HYPOTHETICAL: No ( i v ) ANTI-SENSE: No ( v i ) ORIGINAL SOURCE: Chemically synthesized ( v i i ) IMMEDIATE SOURCE: Chemically synthesized ( i x ) FEATURE:
        ( A ) NAME/KEY: sticky end
        ( B ) LOCATION: bases 1-4

( i x ) FEATURE:
        ( A ) NAME/KEY: duplex
        ( B ) LOCATION: bases 5-35 and bases 91-121
        ( D ) OTHER INFORMATION: Duplex forms intramolecularly ( i x ) FEATURE:
        ( A ) NAME/KEY: single-stranded loop
        ( B ) LOCATION: bases 36-90

( x i ) SEQUENCE DESCRIPTION: SEQ ID NO:2:

GATCCCGGGT ACCATGGCCA AGCTTAAGTA CTCGCTTTTG GGTTAGGAGA GCAGCATCTG 60

ACGACGGAGA TGACGGAAAT GAAAACGACG GCGAGTACTT AAGCTTGGCC ATGGTACCCG 120

G 121

( 2 ) INFORMATION FOR SEQ ID NO:3:

( i ) SEQUENCE CHARACTERISTICS:
        ( A ) LENGTH: 341 Base pairs
        ( B ) TYPE: Nucleic Acid
        ( C ) STRANDEDNESS: Double- Stranded
        ( D ) TOPOLOGY: Linear ( i i ) MOLECULE TYPE: Other nucleic acid
        ( A ) DESCRIPTION: Fragment purified from gel ( i i i ) HYPOTHETICAL: No ( i v ) ANTI-SENSE: No ( v i ) ORIGINAL SOURCE:
        ( A ) ORGANISM: Escherichia coli ( v i i ) IMMEDIATE SOURCE: Sau3A I fragment of pUC18

( v i i i ) POSITION IN GENOME: Nucleotides 1662 to 2003 of pUC18

( i x ) FEATURE:
        ( A ) NAME/KEY: Ava II site
        ( B ) LOCATION: Bases 176-180

( i x ) FEATURE:
        ( A ) NAME/KEY: 21-base primer target site
        ( B ) LOCATION: Bases 1-21

( i x ) FEATURE:
        ( A ) NAME/KEY: 30-base primer target site
        ( B ) LOCATION: Bases 213-242

( x i ) SEQUENCE DESCRIPTION: SEQ ID NO:3:

```
GATCTGTCTA  TTTCGTTCAT  CCATAGTTGC  CTGACTCCCC  GTCGTGTAGA  TAACTACGAT   60
ACGGGAGGGC  TTACCATCTG  GCCCCAGTGC  TGCAATGATA  CCGCGAGACC  CACGCTCACC  120
GGCTCCAGAT  TTATCAGCAA  TAAACCAGCC  AGCCGGAAGG  GCCGAGCGCA  GAAGTGGTCC  180
TGCAACTTTA  TCCGCCTCCA  TCCAGTCTAT  TAATTGTTGC  CGGGAAGCTA  GAGTAAGTAG  240
TTCGCCAGTT  AATAGTTTGC  GCAACGTTGT  TGCCATTGCT  ACAGGCATCG  TGGTGTCACG  300
CTCGTCGTTT  GGTATGGCTT  CATTCAGCTC  CGGTTCCCAA  C                       341
```

( 2 ) INFORMATION FOR SEQ ID NO:4:

( i ) SEQUENCE CHARACTERISTICS:
        ( A ) LENGTH: 30 Bases
        ( B ) TYPE: Nucleic acid
        ( C ) STRANDEDNESS: Single- Stranded
        ( D ) TOPOLOGY: Linear ( i i ) MOLECULE TYPE: Other nucleic acid
        ( A ) DESCRIPTION: BDA Primer ( i i i ) HYPOTHETICAL: No ( i v ) ANTI-SENSE: No ( v i ) ORIGINAL SOURCE: Chemically synthesized ( v i i ) IMMEDIATE SOURCE: Chemically synthesized ( i x ) FEATURE:Complementary to bases 1903 to 1874 of pUC18

( x i ) SEQUENCE DESCRIPTION: SEQ ID NO:4:

```
AACTACTTAC  TCTAGCTTCC  CGGCAACAAT                                       30
```

( 2 ) INFORMATION FOR SEQ ID NO:5:

( i ) SEQUENCE CHARACTERISTICS:
        ( A ) LENGTH: 267 bases
        ( B ) TYPE: Nucleic Acid
        ( C ) STRANDEDNESS: Both Single- Stranded and Double-Stranded
            Regions
        ( D ) TOPOLOGY: Linear ( i i ) MOLECULE TYPE: Other nucleic acid
        ( A ) DESCRIPTION: BDA Adapter ( i i i ) HYPOTHETICAL: No ( i v ) ANTI-SENSE: No ( v i ) ORIGINAL SOURCE:
        ( A ) ORGANISM: Escherichia coli ( v i i ) IMMEDIATE SOURCE: 267-base EcoRI fragment of pIR8 or chemically
            synthesized ( i x ) FEATURE:
        ( A ) NAME/KEY: Duplex region
        ( B ) LOCATION: Bases 6-56 and bases 217-267
        ( D ) OTHER INFORMATION: Duplex forms intramolecularly ( i x ) FEATURE:
        ( A ) NAME/KEY:Loop region
        ( B ) LOCATION: Bases 57-216

( x i ) SEQUENCE DESCRIPTION: SEQ ID NO:5:

```
GAATTCGAGC  TCGGTACCCG  GGGATCCTCT  AGAGTCGACC  TGCAGGCATG  CAAGCTCGCC   60
ATTCGCCATT  CAGGCTGCGC  AACTGTTGGG  AAGGGCGATC  GGTGCGGGCC  TCTTCGCTAT  120
TACGCCAGCT  GGCGAAAGGG  GGATGTGCTG  CAAGGCGATT  AAGTTGGGTA  ACGCCAGGGT  180
```

TTTCCCAGTC ACGACGTTGT AAAACGACGG CCAGTAAGCT TGCATGCCTG CAGGTCGTCT    240

CTAGAGGATC CCCGGGTACC GAGCTCG    267

( 2 ) INFORMATION FOR SEQ ID NO:6:

( i ) SEQUENCE CHARACTERISTICS:
        ( A ) LENGTH: 224 bases
        ( B ) TYPE: Nucleic Acid
        ( C ) STRANDEDNESS: Both Single- Stranded and Double-Stranded
            Regions
        ( D ) TOPOLOGY: Linear ( i i ) MOLECULE TYPE: Other nucleic acid
        ( A ) DESCRIPTION: BDA Adapter ( i i i ) HYPOTHETICAL: No ( i v ) ANTI-SENSE: No ( v i ) ORIGINAL SOURCE:
        ( A ) ORGANISM: Escherichia coli ( v i i ) IMMEDIATE SOURCE: 224-base gel-purified fragment of pIR8 or
            chemically synthesized ( i x ) FEATURE:
        ( A ) NAME/KEY: Duplex region
        ( B ) LOCATION: Bases 5-34 and bases 195-224
        ( D ) OTHER INFORMATION: Duplex forms intramolecularly ( i x ) FEATURE:
        ( A ) NAME/KEY: Loop region
        ( B ) LOCATION: Bases 35-194

( x i ) SEQUENCE DESCRIPTION: SEQ ID NO:6:

GATCCTCTAG AGTCGACCTG CAGGCATGCA AGCTCGCCAT TCGCCATTCA GGCTGCGCAA    60

CTGTTGGGAA GGGCGATCGG TGCGGGCCTC TTCGCTATTA CGCCAGCTGG CGAAAGGGGG    120

ATGTGCTGCA AGGCGATTAA GTTGGGTAAC GCCAGGGTTT TCCCAGTCAC GACGTTGTAA    180

AACGACGGCC AGTAAGCTTG CATGCCTGCA GGTCGTCTCT AGAG    224

( 2 ) INFORMATION FOR SEQ ID NO:7:

( i ) SEQUENCE CHARACTERISTICS:
        ( A ) LENGTH: 30 Bases
        ( B ) TYPE: Nucleic acid
        ( C ) STRANDEDNESS: Single- Stranded
        ( D ) TOPOLOGY: Linear ( i i ) MOLECULE TYPE: Other nucleic acid
        ( A ) DESCRIPTION: Chemically synthesized ( i i i ) HYPOTHETICAL: No ( i v ) ANTI-SENSE: No ( v i ) ORIGINAL SOURCE: Chemically synthesized ( v i i ) IMMEDIATE SOURCE: Chemically synthesized ( x i ) SEQUENCE DESCRIPTION: SEQ ID NO:7:

AACTACTTAC TCTAGCTTCC CGGCAACAAT    30

( 2 ) INFORMATION FOR SEQ ID NO:8:

( i ) SEQUENCE CHARACTERISTICS:
        ( A ) LENGTH: 21 Bases
        ( B ) TYPE: Nucleic acid
        ( C ) STRANDEDNESS: Single- Stranded
        ( D ) TOPOLOGY: Linear (ii) MOLECULE TYPE: Other nucleic acid
    (A) DESCRIPTION: BDA Primer (iii) HYPOTHETICAL: No (iv) ANTI-SENSE: No (vi) ORIGINAL SOURCE: Chemically synthesized (vii) IMMEDIATE SOURCE: Chemically synthesized (xi) SEQUENCE DESCRIPTION: SEQ ID NO:8:

GATCTGTCTA TTTCGTTCAT C                                                       21

(2) INFORMATION FOR SEQ ID NO:9:

(i) SEQUENCE CHARACTERISTICS:
    (A) LENGTH: 27 Bases
    (B) TYPE: Nucleic acid
    (C) STRANDEDNESS: Single-Stranded
    (D) TOPOLOGY: Linear (ii) MOLECULE TYPE: Other nucleic acid
    (A) DESCRIPTION: Chemically synthesized (iii) HYPOTHETICAL: No (iv) ANTI-SENSE: No (vi) ORIGINAL SOURCE: Chemically synthesized (vii) IMMEDIATE SOURCE: Chemically synthesized (xi) SEQUENCE DESCRIPTION: SEQ ID NO:9:

AAACGACGGC GAGTAATGAA CTAAACG                                                 27

(2) INFORMATION FOR SEQ ID NO:10:

(i) SEQUENCE CHARACTERISTICS:
    (A) LENGTH: 147 Base pairs
    (B) TYPE: Nucleic Acid
    (C) STRANDEDNESS: Double-Stranded
    (D) TOPOLOGY: Linear (ii) MOLECULE TYPE: Genomic DNA (iii) HYPOTHETICAL: No (iv) ANTI-SENSE: No (vi) ORIGINAL SOURCE:
    (A) ORGANISM: Arabidopsis thaliana (vii) IMMEDIATE SOURCE: BDA-generated region of Arabidopsis thaliana
                genomic DNA using primer of SEQ ID NO:9

(viii) POSITION IN GENOME: Unknown (ix) FEATURE:
    (A) NAME/KEY: Primer identity
    (B) LOCATION: Bases 1-27

(xi) SEQUENCE DESCRIPTION: SEQ ID NO:10:

AAACGACGGC GAGTAATGAA CTAAACGTGT TCTTGTGACG AAGGGCGAGA GAACTCGCCT     60

TTTTTATTTA AGATAACAGT GCGTGTTGTT GCGTCTTTTG CAGCATTTCG GAGGTATGAC   120

TACCGATAAA GAACTGCCGC AACCTGG                                                147

(2) INFORMATION FOR SEQ ID NO:11:

(i) SEQUENCE CHARACTERISTICS:

-continued (A) LENGTH: 114 Base pairs
(B) TYPE: Nucleic Acid
(C) STRANDEDNESS: Double- Stranded
(D) TOPOLOGY: Linear (ii) MOLECULE TYPE: Genomic DNA (iii) HYPOTHETICAL: No (iv) ANTI-SENSE: No (vi) ORIGINAL SOURCE:
(A) ORGANISM: Arabidopsis thaliana (vii) IMMEDIATE SOURCE: BDA-generated region of Arabidopsis thaliana
genomic DNA using primer of SEQ ID NO:9

(viii) POSITION IN GENOME: Unknown (ix) FEATURE:
(A) NAME/KEY: Sau3A Sticky End
(B) LOCATION: Bases 1-4

(xi) SEQUENCE DESCRIPTION: SEQ ID NO:11:

```
GATCAGGTAA GTATCATCTC AAGTTTATCT CGTGGTTCTC TGTGTTTACT TTTTTGAAGT    60

TCTCAGGCTT CAATGGAAAT ACTTCTCCCC TTTGAAATGT GTGTAGGAGA ATAA         114
```

BOOMERANG DNA AMPLIFICATION

This is a continuation of application Ser. No. 07/841,320, filed Feb. 20, 1992 abandoned.

FIELD OF THE INVENTION

The present invention pertains to recombinant DNA technology.

BACKGROUND OF THE INVENTION

The current method of choice for amplifying specific target DNA sequences is the Polymerase Chain Reaction (PCR) technique described generally in Mullis et al., U.S. Pat. No. 4,683,195. General features of PCR are shown schematically in FIG. 1. One begins with double-stranded DNA 10 containing a sequence of interest 12. The sequence of interest 12 is flanked by "primer target" sequences 14, 16. Primers 18, 20 are added to the DNA 10 along with a DNA polymerase and deoxyribonucleoside triphosphates. (Usually, a heat-stable DNA polymerase is employed to ensure that the polymerase activity is not destroyed by the heating required for denaturation.) The primers 18, 20 are single-stranded DNA oligonucleotides having sequences complementary to the primer target sequences 14, 16, respectively. The resulting mixture is heated to denature the DNA 10. After denaturation, the mixture is cooled sufficiently to allow the primers 18, 20 to anneal to the primer target sequences 14, 16, respectively, forming primed duplexes 21, 22, respectively. The primed duplexes 21, 22 are capable of being enzymatically extended. Since the polarity of each primer 18 is opposite the polarity of the other primer 20, replication of the sequence of interest 12, beginning from the 3' end of each primer 18, 20, will occur on both target strands 12a, 12b, respectively, of the sequence of interest 12. (In FIG. 1, the arrows 23, 24 denote the replication direction of primed duplexes 21 and 22.) During a "cycle" of replication, a strand complementary to each strand 12a, 12b of the sequence of interest is synthesized, wherein each strand 12a produces a complementary strand 12b (along with primer target 16) and each strand 12b produces a complementary strand 12a (along with primer target 14). After each cycle of replication, the reaction mixture is heated to denature the newly synthesized strands from their complementary parent strands. This cycle is repeated as many times as necessary to obtain the desired quantity of DNA of the sequence of interest 12. During each cycle of replication, primers anneal not only to the strands from the original sequence of interest, but also to strands produced by each round of replication. Thus, the number of copies of the sequence of interest 12 substantially doubles during each cycle. After multiple cycles, a large amount of the DNA from the sequence of interest 12 is produced that can be sequenced, cloned, or visualized on a gel.

Although PCR empowers users to amplify nucleic acid sequences exponentially, it has certain drawbacks. For example, replication from each primer must proceed in the direction of the primer on the complementary strand. Thus, only sequences located between primer target sequences can be amplified by PCR. However, it is often necessary or desirable to amplify sequences located outside a region flanked by primer target sequences.

Another disadvantage of PCR is that it requires two primers, thereby requiring that the practitioner have a detailed knowledge of sequences found in two separate regions near the sequence of interest. This information is not always available or readily obtainable.

SUMMARY OF THE INVENTION

The present invention, termed "Boomerang DNA Amplification" (BDA), provides an alternative DNA amplification method to PCR. A key advantage of BDA is that DNA amplification can be performed using only one primer. As a result, the DNA that is amplified using BDA is not limited to a region of the DNA situated between two primers. Thus, BDA allows extremely long DNA sequences to be quickly determined by performing a "round" of BDA on each of a series of overlapping regions in the DNA. BDA can also be conveniently used for cloning DNA.

The BDA method begins with cleaving a sample DNA so as to form discrete linear duplex fragments having ligatable ends (wherein the term "duplex" denotes complementary ends of DNA hydrogen-bonded to each other in a standard Watson-Crick manner as known in the art.) Preferably, such cleavage is performed using a restriction endonuclease that generates discrete fragments of the DNA having what are known in the art as "sticky ends." The agent used to cleave the DNA is selected such that, among the various duplex fragments of DNA produced thereby, at least one of the fragments will comprise a sequence of interest (SOI) and a primer target site associated therewith.

The sequence of the SOI need not be known beforehand. The sequence of the primer target site must be at least partially known, as determinable from other data such as an amino-acid sequence of the corresponding protein or from sequencing studies of regions of the DNA beginning at locations upstream of the primer target site. Knowing at least a portion of the primer target site permits an appropriate primer, homologous to the primer target site, to be prepared for use in BDA. The primer target site can be located within a SOI or flanking the SOI.

Because the fragments containing the SOI are linear duplexes, the SOI in such fragments comprise a first region (in this case, a first "strand") and a second region (a second "strand") complementary to the first region.

The duplex fragments are ligated to "adapter" molecules. Adapters are polynucleotides (either single-stranded or double-stranded) containing internal sequences complementary to each other that are capable of annealing to each other to form a duplex under appropriate conditions. Single-stranded adapters have a single-stranded loop on a first end and an opposing second end ligatable to the fragments of cleaved sample DNA. Double-stranded adapters contain internal sequences complementary to each other, preferably located at the ends of the adapters. At least one end of double-stranded adapters is ligatable to cleaved sample DNA. Ligation of adapters is performed under "ligation conditions" wherein an adapter is coupled to each end of the duplex fragments, thereby forming templates usable for BDA. Usually, a DNA ligase is used. As used herein, a "BDA template" is defined generally as a DNA sequence that comprises at least a primer sequence and an adapter sequence.

Oligonucleotide primers homologous to the primer target site are added to the BDA templates. Because the primers bind only to BDA templates possessing a primer target site, only such templates will be amplified in the BDA reaction. A DNA polymerizing agent such as a DNA polymerase is also added along with the usual dNTPs in a suitable buffer. Preferably, the DNA polymerase is thermostable (to denaturation temperatures) so that all the required enzymatic activity can be added to the BDA reaction at one time.

In a typical BDA "cycle," the resulting mixture is heated to a temperature suitable to denature the BDA templates, then cooled to a range typical of "hybridizing conditions" to allow complementary sequences to anneal to each other, such as the primers to anneal to the primer target sites on the BDA templates. Each primer is then "extended" under DNA replication conditions in which the DNA polymerizing agent is active and dNTPs are incorporated into a primer-extension product, complementary to the BDA template, that grows from and includes the primer. Thus, primer extension forms a duplex on the BDA template. In order to proceed further with BDA, each such primer extension product must have incorporated sequences complementary to at least a portion of each of the first and second self-complementary sequences of an adapter. Preferably, particularly when using single-stranded adapters, primer extension is allowed to proceed past a sequence on the BDA template that is complementary to the primer target site. After primer extension, the duplex products are denatured.

Typically, multiple such "cycles" are performed until the desired amount of SOI DNA is produced. A "round" of BDA is comprised of one or more cycles all employing the same primer. Afterward, the DNA is typically size-fractionated on a gel. The amplified DNA can then be used for sequencing, cloning, or other use. As described in further detail herein, BDA cloning is an example wherein a round typically comprises only one cycle.

For sequencing a large DNA, multiple "rounds" of BDA can be performed, wherein each round is directed to amplifying a particular segment of the DNA, preferably in a sequential segment-by-segment manner ("walking" down the DNA). Each such round comprises a number of cycles sufficient to achieve the desired amount of amplification. The DNA obtained in each round is sequenced using conventional methods. In each round, the primer target site for use in the subsequent round is obtained from the sequence information obtained using DNA amplified in the preceding round. As a result, the primer target site used in the subsequent round is located downstream of the primer target site used in the preceding round and different primers are used in each round. Also, the DNAs amplified in each round overlap, thereby allowing registration of sequences of the DNAs amplified in several rounds. Such registration permits accurate sequences of very long DNAs to be determined.

BDA can also be used for cloning a DNA sequence of interest. In such a method, adapters are ligated to compatible DNA fragments at least some of which contain an SOI and a primer target site. The adapters include an origin of replication and a selectable marker. Also, in each cycle, primer extension is performed for a time sufficient to produce primer extension products that extend along the entire BDA template, thereby forming duplexes that include the SOI, the origin of replication, and the selectable marker. Subsequent treatment using a single-strand-specific endonuclease will not degrade the duplexes but will damage other DNAs present. Subsequent transformation of susceptible host cells results in cloning of the duplexes.

BRIEF DESCRIPTION OF THE DRAWINGS

FIG. 3A schematically shows beginning steps in a BDA process according to the present invention, wherein sample DNA containing a sequence of interest is cleaved using a restriction endonuclease and "panhandled" adapters are attached to the resulting fragments of the sample DNA, thereby forming closed-loop structures.

FIG. 3B is a continuation of FIG. 3A showing further steps in a BDA process using panhandled adapters, wherein a primer is annealed to each closed-loop structure that contains a primer target sequence and subsequent primer extension results in duplication of at least a portion of the sequence of interest.

DETAILED DESCRIPTION

Boomerang DNA Amplification (BDA) according to the present invention provides a way to amplify a DNA sequence of interest when only one primer region associated with the sequence of interest is known. BDA also permits amplification of sequences that would otherwise reside outside a region suitable for PCR. As used herein, to "amplify" a DNA sequence of interest means to increase the amount of said sequence relative to other DNA sequences that may also be present.

BDA employs "adapters." Adapters are single-stranded or double-stranded polynucleotides that have internal sequences complementary to each other that are capable of annealing to each other to form a duplex under appropriate conditions. Such sequences are termed "self-complementary sequences" or "SCSs."

Figure 1:
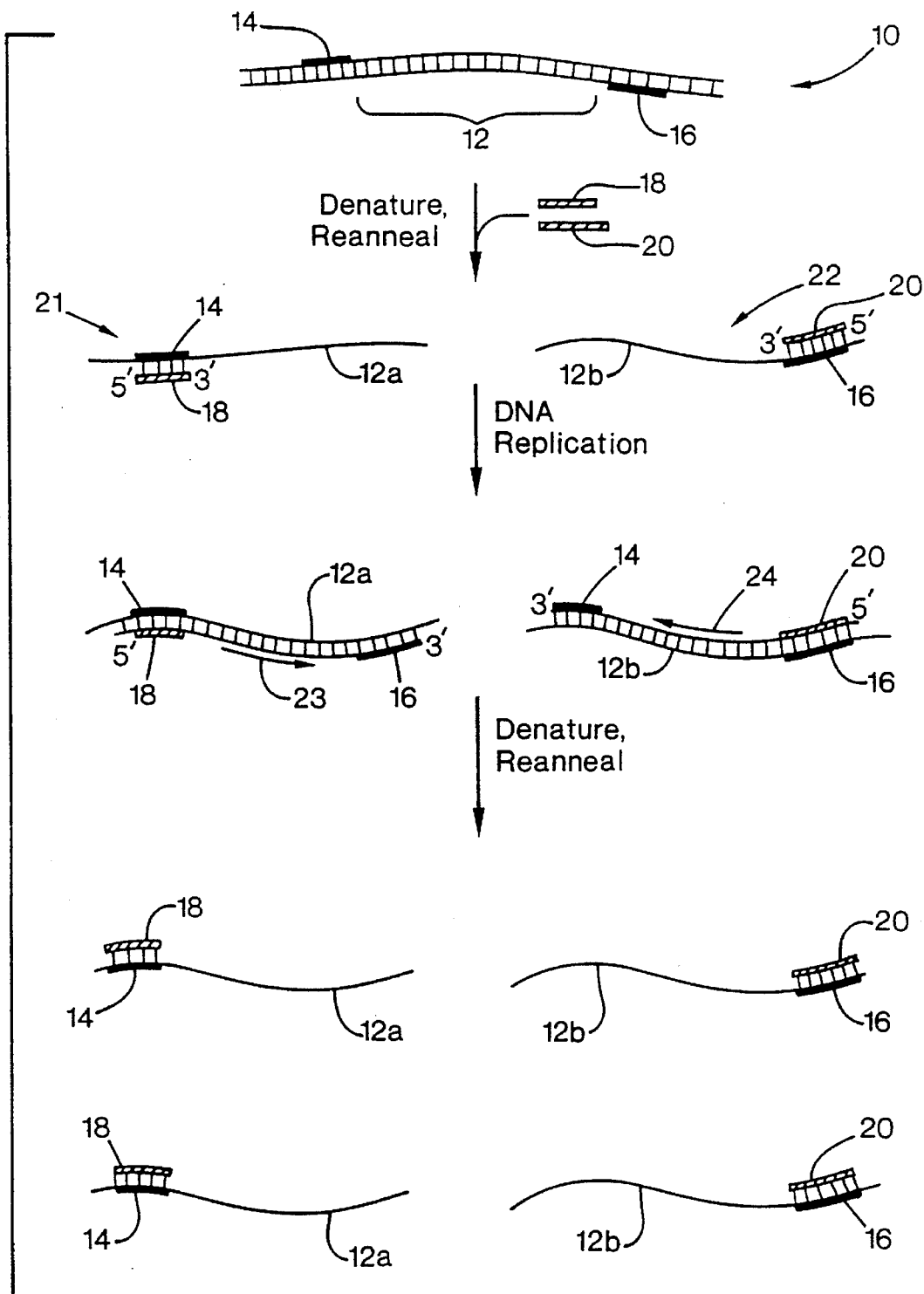
FIG. 1 schematically depicts the amplification of DNA using the prior art PCR method.
Figure 2A:
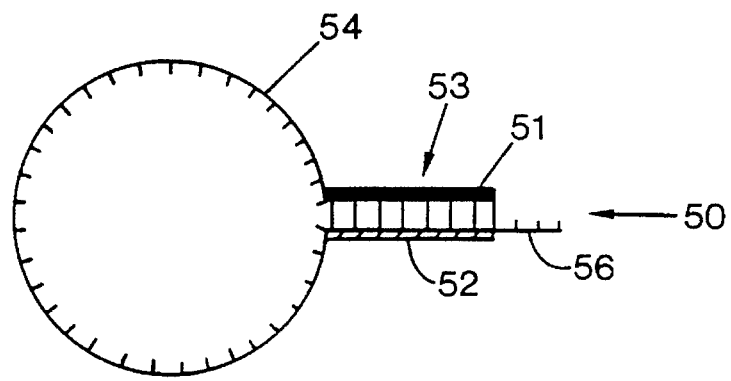
FIG. 2A schematically shows a single-stranded (or "panhandled") adapter molecule according to the present invention usable for performing Boomerang DNA Amplification (BDA).

One type of adapter 50, termed a single-stranded (or "panhandled") adapter, is shown schematically in FIG. 2A. The adapter 50 has a first SCS 51 and a second SCS 52 that may anneal to each other to form a duplex structure 53 resembling a "panhandle." A "spacer" region 54 is situated between the first and second SCSs 51, 52. Because the spacer 54 is not complementary to other sequences of the adapter 50, it forms a single-stranded loop on one end of the panhandle 53. The opposing end of the panhandle 53 is "ligatable" (i.e., able to be enzymatically coupled) to a similar end on either another adapter or a fragment generated by cleavage of DNA. Preferably, the ligatable end is a "sticky" end 56, meaning that said end is capable of annealing and being ligated to complementary sticky-ended DNA fragments generated by cleavage of DNA using a restriction endonuclease.

Figure 2B:
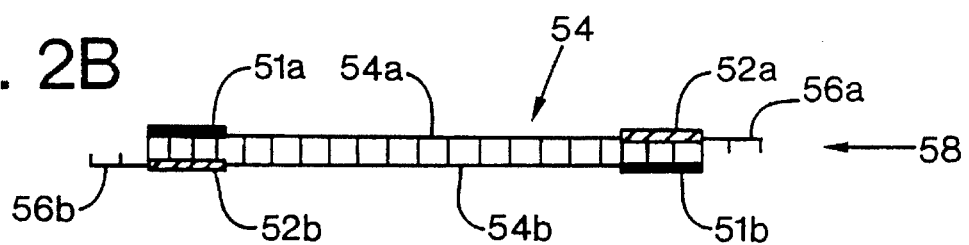
FIG. 2B schematically shows a double-stranded adapter molecule according to the present invention usable for performing BDA.

Another type of adapter, termed a "double-stranded" adapter 58, is shown schematically in FIG. 2B, wherein features that are identical to features shown in FIG. 2A have the same reference designators (with suffixes "a" or "b" to distinguish complementary strands). Double-stranded adapters have SCSs 51a, 52a, and 51b, 52b, wherein one of said sequences is preferably located at each end of the adapter 58. It is also possible for the SCSs 51a, 52a, 51b, 52b to not be located on the ends of the double-stranded adapter 58, but such a configuration is not preferred for BDA because it is less efficient. The double-stranded adapter 58 also comprises a "spacer" region 54 comprising strands 54a and 54b, wherein the spacer strand 54a is situated between the self-complementary sequences 51a and 52a, and the spacer strand 54b is situated between the self-complementary sequences 51b and 52b. Double-stranded adapters are generally fully duplex except for a single-stranded overhang 56a, 56b on at least one end as may be desirable for making the end "sticky" for ease of ligation. In any event, at least one end of the double-stranded adapter 58 is "ligatable."

Figure 2C:
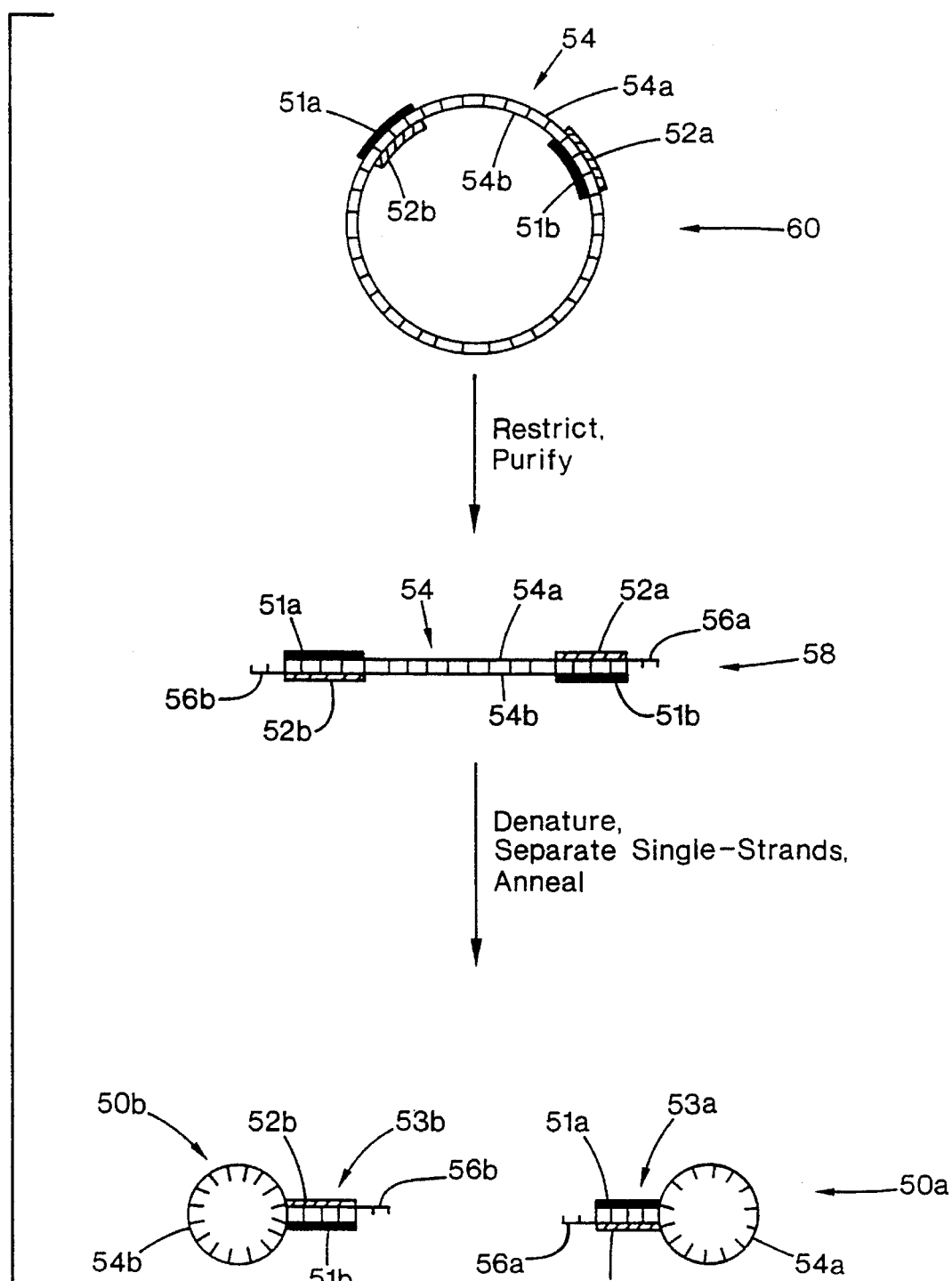
FIG. 2C schematically shows a way in which double-stranded adapters and single-stranded adapters can be synthesized.

As shown in FIG. 2C, double-stranded adapters 58 are convertible into panhandled adapters 50a, 50b by denaturing the double-stranded adapters 58, isolating the resulting single strands, and self-annealing the single strands.

In either panhandled or double-stranded adapters, the size of the spacer 54 is not critical and is preferably kept somewhat small for reasons of economy. Preferably, the spacer 54 is at least 10–15 bases long, up to about 200 bases long. Larger spacers will work but may require BDA production of excess unneeded DNA (which can either prematurely exhaust the supply of primers, dNTPs, and DNA polymerase in the BDA reaction or necessitate the addition of extra amounts of expensive primers, dNTPs, and DNA polymerase). Spacers smaller than 10–15 bases, including hairpin loops (0–3 bases) formed by contiguous self-complementary ends, should also work, but their use may result in unpredictable products due to the interaction of the DNA polymerase with the unusual structure posed by single-stranded nucleic acids tightly bent in this manner.

In the following description of adapters, the suffixes "a" and "b" are not used with reference designators 50, 51, 52, 54, and 56 for the sake of brevity. However, it will be understood that, where applicable and unless otherwise indicated, said discussion applies to both panhandled and double-stranded adapters.

The SCSs 51, 52 may be comprised of one or more polylinker DNA sequences. As used herein, a "polylinker" is a region of DNA composed of tightly clustered multiple restriction sites. A polylinker is also referred to in the art as a "polylinker cloning site." The SCSs 51, 52 can have any of a wide variety of different polylinker DNA sequences, thereby enabling one to have great latitude in selecting an appropriate sticky end for annealing the adapters to ends of DNA fragments generated using different restriction endonucleases. Also, multiple restriction sites in the polylinkers facilitate downstream cloning of DNA amplified by BDA. However, it is also possible for the SCSs 51, 52 to have only one restriction site or only an end compatible for ligation to other restricted DNAs and still be useful for BDA.

SCSs 51, 52 usually have a length of at least about 15–20 base pairs (bp). This length is the minimal length normally required for SCSs to form a duplex at room temperature. While SCSs can have lengths as long as 100 to 200 bases, or longer, it is preferred for reasons of economy to not use SCSs that are longer than necessary.

Both panhandled adapters 50 and double-stranded adapters 58 can be generated from circular or linear DNAs by any of several possible methods. FIG. 2C is a schematic diagram showing a way in which adapters can be generated from a circular duplex DNA 60. (An example of another possible method for generating adapters is described in Example 1.) The circular DNA 60 comprises a first SCS duplex 51a, 52b, and a second SCS duplex 51b, 52a. The SCS duplex 51a, 52b has a sequence substantially identical to the SCS duplex 51b, 52a but in the opposite orientation. Thus, the SCSs 51a, 52a are complementary to each other in the same strand. Likewise, the SCSs 51b, 52b are complementary to each other in the same strand. It will also be appreciated that SCS 51a is substantially identical to SCS 51b and SCS 52a is substantially identical to SCS 52b. A spacer region 54 is situated between the SCS duplexes. The spacer 54 is preferably at least 10 to 15 bp long. The duplex circular DNA 60 is cleaved using a restriction endonuclease that preferably cuts at a locus adjacent each SCS duplex 51a, 52b and 51b, 52a. Subsequent gel purification yields the double-stranded adapter 58, as described above. Subsequent separation of the single strands on a denaturing gel and self-annealing yields the corresponding panhandled adapters 50a, 50b. Each double-stranded adapter has a sticky end 56a, 56b on each end thereof, and each panhandled adapter 50a, 50b has a sticky end 56a, 56b, respectively.

It is also possible for the adapters to have blunt, rather than sticky, ligatable ends. However, attachment of adapters having blunt ends to other pieces of DNA so as to practice BDA is inefficient compared to attachment of sticky-ended adapters.

Figure 3C:
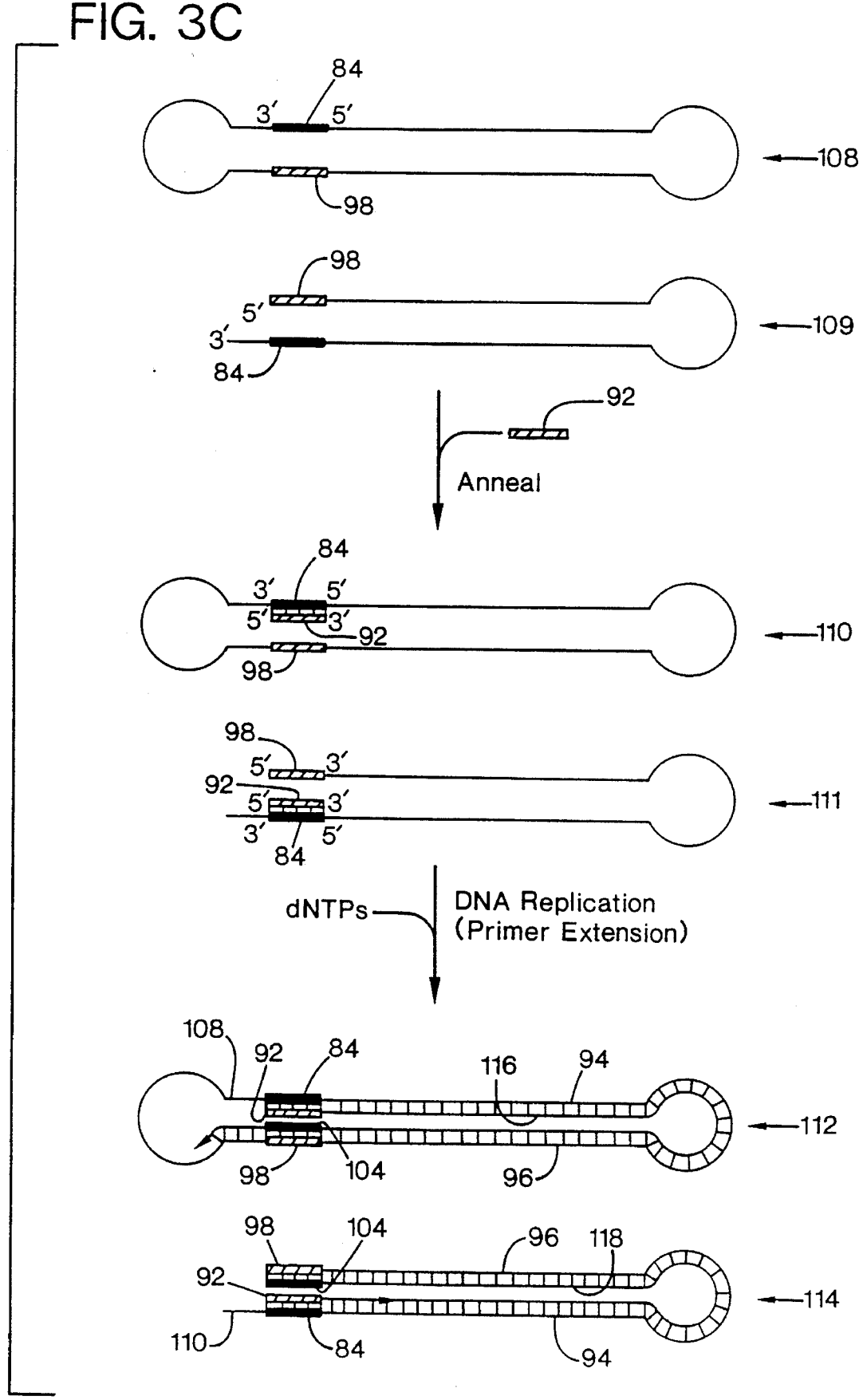
FIG. 3C is a continuation of FIG. 3B showing steps in a subsequent cycle of DNA amplification via BDA using panhandled adapters.

A general sequence of events in BDA, using only one primer and panhandled adapters 50, is illustrated schematically in FIGS. 3A–3D. Referring first to FIG. 3A, BDA begins with a sample DNA 80 usually comprising a number of DNA sequences but also containing a sequence of interest (SOI) 82 to be amplified. For example, the sample DNA 80 can comprise genomic DNA. The SOI 82 can have any of a variety of lengths. Although, in principle, there is no limit to the length of the SOI 82, BDA (like PCR) is more difficult to perform if the SOI 82 is longer than about 4 kilobases (kb). Longer SOI sequences can cause premature exhaustion of BDA reaction constituents (such as DNA polymerase, dNTPs, or primers), or untimely drop-off of DNA polymerase enzyme molecules from the DNA being amplified.

The SOI 82 can either span a primer target site (comprising sequence 84) or be situated adjacent the primer target site 84, as shown in FIG. 3A. For best BDA results, the primer target site 84 should be uniquely associated with the SOI 82. The primer target site 84 is selected using criteria similar to criteria used in selecting primer target sites for PCR. For example, if the SOI 82 belongs to a group of related genes in other organisms or to a family of related genes in the same organism, wherein the sequence of another gene in the group or family is entirely or partially known, a possible primer target site 84 can be ascertained from said sequence. Alternatively, if the sequence of a polypeptide encoded by the SOI 82 is at least partially known, possible primer target sites can be ascertained using the genetic code (and allowing for the degeneracy of the code). Another way in which a primer target site 84 can be selected is by selecting a known conserved or "consensus" region upstream of a particular gene, such as a promoter.

As can be surmised from its name, the primer target site 84 serves as a region to which a complementary single-stranded primer of the same length will bind (anneal). The primer target site 84 should have a length sufficient to form a stable duplex with a complementary primer at the annealing temperature of the BDA reaction. In general, a minimal length satisfying this criterion is about 15 to 20 bases long. The primer target site should also have sufficient length to be "discriminating," i.e., to ensure that the primer binds substantially only to it and not to other sequences as well. As is known in the art, longer primers are more discriminating than short primers in their binding of target sequences when appropriate conditions for annealing are employed. I have found that primer target sites of about 30 bases long exhibit satisfactory discriminatory binding to complementary primers. Longer primer target sites can be used, but other reasons, such as economy or simply lack of sequence information about any more of the SOI 82 usually preclude such use.

It will be appreciated that primer length is ideally equal to the length of the corresponding primer target site 84, but in some cases can (and may) vary slightly. Primers can be conveniently made using a conventional DNA oligonucleotide synthesizer.

The sample DNA 80 is cleaved preferably using either the same restriction endonuclease used to create the adapter 50 or any other restriction endonuclease that creates sticky ends 86 homologous to the sticky ends 56 on the adapters 50. Such cleavage yields a number of DNA fragments each terminating with a sticky end 86. Some fragments 87 contain the primer target site 84 and the SOI 82. A relatively large number of other fragments 88 lack the SOI 82 and, consequently, the primer target site 84.

An excess amount of adapters 50 is added to the cleaved sample DNA under conditions wherein the sticky ends 56 of the adapters 50 anneal to the sticky ends 86 of the cleaved sample DNA. "Excess" in this context refers to a number of adapter sticky ends 56 greater than the total number of sticky ends 86 represented by the population of cleaved sample DNA. The number of sticky ends represented by the cleaved sample DNA can be approximated by persons skilled in the art by knowing the approximate molecular weight of uncleaved sample DNA, the particular site at which the restriction enzyme cleaves the sample DNA, the AT/GC composition of the sample DNA, and the actual amount of sample DNA to be cleaved. Preferably, "excess" means at least about an 8:1 ratio of adapter sticky ends 56 to cleaved-sample-DNA sticky ends 86, to greater than about 100:1. Too low a ratio can result in cleaved sample DNA pieces annealing to themselves rather than to adapters, decreasing the efficiency of BDA. The annealing of excess adapters to themselves causes no problem in BDA (other than a decrease in efficiency) because such annealed molecules are not primable when proper annealing conditions and primer sequences are employed.

Annealing of adapters 50 to cleaved sample DNA is performed at a relatively low temperature, such as within a range of about 0° C. to about 25° C., typically about 16° C.

A DNA ligase (such as T4 DNA ligase obtainable from New England BioLabs, Inc., Beverly, Mass., and used according to the manufacturer's directions) is used to covalently bond the adapters 50 to the fragments of sample DNA to form a population 89 of various "closed-loop structures." The closed-loop structures, as can be seen, comprise a length of duplex DNA terminated on each end by a loop 54 contributed by the adapter 50. Although potentially all the restriction fragments of the sample DNA can form closed-loop structures 89, at least one group 90 of the closed-loop structures includes the primer target site 84 and the SOI 82 and can therefore serve as a BDA template. It will be appreciated that T4 DNA ligase can ligate blunt ends. Thus, again, blunt-ended adapters can be used to perform BDA. Another possible DNA ligase is *E. coli* DNA ligase (also obtainable from New England BioLabs). However, this ligase cannot ligate blunt ends.

Once the closed-loop structures 89 are prepared, other ingredients (reactants) are added thereto to prepare a reaction mixture. The reaction mixture preferably contains sufficient amounts of reactants so that an entire "round" of BDA comprising multiple cycles of amplification of the SOI 82 can occur without having to replenish the reactants part way through the round. Reaction conditions for BDA should closely approximate buffer requirements of the DNA polymerase employed. A representative BDA reaction mixture comprises the population 89 of closed-loop structures, primers 92, buffer (such as 10 to 50 mM Tris-HCl buffer, pH about 8.3 to about 8.8 at 25° C.) all four dNTPs (in equal concentrations to minimize misincorporation errors, wherein the concentration of each dNTP ranges between 20 to 200 µM), a DNA polymerizing agent such as a DNA polymerase, and a magnesium salt such as magnesium chloride or magnesium sulfate (depending on the DNA polymerase used).

The DNA polymerase employed is preferably a "thermostable" DNA polymerase capable of withstanding denaturation temperatures. Examples of thermostable polymerases include the well-known Taq DNA polymerase and Vent™ DNA polymerase (available from New England BioLabs, Beverly, Mass.) which can withstand nearly boiling temperatures such as 95° C. (or higher for Vent™ DNA polymerase). Less thermostable DNA polymerases can also be used, but may require replenishment after each cycle. An example of the latter is the Klenow fragment of *E. coli* DNA polymerase.

As a first approximation, the amount of DNA polymerase added to the reaction mixture can be according to the enzyme manufacturer's suggestions. However, the amount actually required in a particular BDA reaction mixture will depend upon several factors, including the type of polymerase, the temperature at which DNA replication will occur, the intended number of replication cycles in the BDA "round," and the combined length of the SOI, polylinkers, and loops. Skilled artisans are familiar with altering the concentration of DNA polymerase in a DNA replication reaction and how to ascertain optimal concentrations of the enzyme.

Depending upon the DNA polymerase used in the reaction, addition of other ingredients (or omission of some of the ingredients described above) may be useful for optimal polymerization. Optional ingredients may include KCl (typically 50 mM or lower), DMSO, gelatin or bovine serum albumin (generally at about 100 µg/mL to stabilize the DNA polymerase), ammonium sulfate (10 mM), magnesium sulfate (5 mM), Triton X-100 (0.1%), or other ingredients depending on the particular DNA polymerase employed.

The amount of primer 92 present in the BDA reaction mixture is a concentration in large excess relative to the concentration of the primer target sequence 84. Preferably, as in PCR, enough primer 92 is added to the reaction mixture to last through the intended number of cycles in the BDA "round." Calculating the amount of primer 92 to add is within the purview of persons skilled in the art having a knowledge of the amount of sample DNA in the BDA reaction mixture and the number of copies of the SOI in the sample DNA. To illustrate the magnitude of the "excess," the molar ratio of primer to primer target sites can be about 30 million or more. Such an excess also helps prevent reannealing of the denatured closed-loop structures 90 with themselves in the region of the priming sequence.

To begin a cycle of DNA replication in a BDA process, the population 89 of closed-loop structures is heated (FIG. 3A), generally at a temperature of about 93° to about 100° C., for a time sufficient for full denaturation (up to about five minutes). The temperature is then lowered to a point where the primers 92 anneal efficiently to the primer target sites 84.

Proper annealing of primers in BDA, like PCR, is regulated by the annealing temperature and the concentration of primers. (As noted above, the concentration of primers may require alteration to effect efficient and accurate priming.) Several factors affect the annealing temperature. These include (but are not necessarily limited to) the primer length, the salt concentration, and the primer base composition (i.e., number of A and T bases relative to number of G and C bases). Persons skilled in the art are familiar with methods for calculating a temperature $T_m$ at which half the primer target sites will have primer molecules annealed thereto. Generally, an applicable annealing temperature is about 5° C. below the $T_m$ of the primers. Thus, annealing temperatures are generally within a range of about 50° C. to about 70° C. The annealing temperature should be high enough to prevent non-specific binding of the primers to the sample DNA. Increasing the annealing temperature generally enhances discrimination against incorrectly annealed primers. As in PCR, some empirical experimentation may be required to ascertain the optimal annealing temperature.

Annealing of primers at a temperature within the stated range occurs rapidly (less than one minute). However, at this beginning stage of BDA wherein primers are annealed to the BDA templates 90 for the first time, more time is usually allowed, generally about two minutes, to ensure that primers bind to the BDA templates 90 as efficiently as possible.

Tetramethylammonium chloride may be added to the reaction mixture to enable one to more accurately predict an effective annealing temperature. As known in the art, this compound equalizes the binding strength of G:C base pairs relative to A:T base pairs, thereby allowing one to more precisely determine and use an annealing temperature that prevents mismatched sequences from hybridizing to form a duplex.

In BDA, it is preferred that only the templates 90 that include the primer target site 84 experience replication. Thus, annealing is performed under conditions wherein the primers 92 anneal substantially only to the primer target sites 84. (For simplicity, closed-loop structures lacking the primer site 84 are not shown further in FIGS. 3A–3D.)

Referring now to FIG. 3B, the primed template 91 is shown having a first region 94 containing a primer target site 84 to which a primer 92 is annealed. The opposing second region 96 (complementary to the first region 94) includes a sequence 98 substantially identical to the primer 92. 5' and 3' ends of the primer target site 84 and primer 92 are denoted to indicate orientation. The primed template 91 also has a "spacer" region 100, 101 located on each end. Each spacer 100, 101 was contributed by a panhandled adapter 50 (FIG. 3A) and was originally the looped spacer 54 of said adapter.

The oligonucleotide primers 92 annealed to the primer target sites 84 serve as initiation sites of DNA replication (replication is also termed "primer extension") during subsequent steps in each cycle. As shown in FIG. 3B, primer extension begins on the 3'-ends of the primers 92 and proceeds in a 5' to 3' direction. Since the primed templates 91 are closed loops, replication can proceed down the first region 94, around a spacer 100, and down the second region 96, thereby generating a primer extension product 102. (The procession of replication around the spacer 100 suggested the motion of a boomerang, hence the coined name of the present method.) It will be appreciated that primer extension continuing past the region 98 generates a new primer target site 104 as part of the primer extension product 102.

Primer extension as described above is allowed to proceed only for a short time during each cycle. The exact point on the primed template 91 where DNA replication stops is not critical, so long as replication has proceeded from the primer 92 down the first region 94, around the spacer 100, and into the second region 96 toward the region 98 a sufficient distance to produce a primer extension product 102 that can form a duplex with itself between a segment thereof complementary to the first region 94 and a segment thereof complementary to the second region 96. Although, under certain conditions, a primer extension product 102 could form such a duplex with the segment complementary to the second region 96 being as small as one base, a stable duplex between a segment complementary to the first region 94 and a segment complementary to the second region 96 would generally require that the segment complementary to the second region be at least about 10 bases long. Preferably, primer extension is allowed to proceed on through the opposing complementary region 98, thereby generating a primer target site 104 on the primer extension product 102.

It will be appreciated by persons skilled in the art that primer extension products that do not include a complementary region 98 can be extended in subsequent BDA cycles. This is because the duplex formable by the primer extension product can, in fact, function as a primed template for DNA replication.

The amount of time required to achieve the requisite amount of DNA replication per cycle is dependent upon several factors of which artisans skilled in PCR are familiar. These factors include the type of DNA polymerase being used, the length and concentration of the primed template 91, and upon the temperature. The temperature, of course, must be suitable for the particular DNA polymerase used. For example, the Vent™ polymerase is typically used at a temperature of about 70° C. to about 76° C. (Higher temperatures may cause the primer to become denatured from the template.) At 72° C., rates at which this enzyme replicates DNA can vary two to three fold, depending upon the buffer, the pH, concentration of salts, and the nature of the template. As a starting point, one minute at 72° C. is often sufficient to produce primer extension products up to about 2 kb in length. Cycling times may be varied to insure the most efficient production of full-length primer extension products. As in PCR, it may be necessary for the skilled artisan to perform preliminary experiments to ascertain minimal amounts of time required to achieve the requisite amount of DNA replication.

The principal disadvantages of allowing DNA replication to proceed for too long is loss of process economy and possible premature exhaustion of the supplies of DNA polymerase and dNTPs in the reaction mixture. Aside from possibly necessitating an unplanned replenishment of DNA polymerase and dNTPs, allowing too much time does no real harm to the outcome of BDA because DNA polymerases, upon progressing once entirely around the primed template 91, will generally drop off the template.

Referring further to FIG. 3B, after the primer extension products 102 are produced, the resulting duplex DNAs 106 are heat-denatured, thereby allowing the template 108 to separate from the primer extension product 109. For maximal BDA efficiency, each of these denatured DNAs 108, 109 has a primer target site 84. Thus, each also has a region 98 complementary to the primer target site 84. (It will be appreciated that the primer target sites 84, 104 are identical. Therefore, on the denatured primer extension product 109, the primer target site 84 now has the same reference designator as the primer target site 84 on the denatured template 108.)

It is desirable that denaturation result in complete separation of the primer extension product 109 from the template 108. Incomplete separation can allow these denatured DNAs to rapidly reanneal together, thereby reducing the ultimate yield of amplified DNA. Typical denaturation conditions comprise a temperature from about 93° C. to about 96° C. (preferably about 95° C.) for one minute or less. Too high a temperature or too long a denaturation time can cause premature exhaustion of the enzyme activity and/or dNTPs in the reaction mixture.

Referring now to FIG. 3C, a subsequent cycle of DNA replication is initiated by annealing primers 92 to the denatured DNAs 108, 109 to form the primed templates 110, 111. The annealing temperature is usually the same as employed previously (about 50° to about 70° C.). However, the annealing time is usually shorter than before, typically about 30 seconds or less. The DNA polymerase in the reaction mixture effects primer extension from the 3'-ends of the primers 92, thereby generating duplex structures 112, 114. The duplex structure 112 comprises the template 108 and a new primer extension product 116. As in the preceding cycle, primer extension is allowed to proceed at least for a time sufficient to produce a primer extension product 116, 118 that can form a duplex with itself between a segment thereof complementary to the first region 94 and a segment thereof complementary to the second region 96. Each primer extension product 116, 118 preferably includes a region 104 having a sequence complementary to the primer 92 and identical to the primer target site 84. Thus, the region 104 can serve as a primer target site in a subsequent BDA cycle.

Figure 3D:
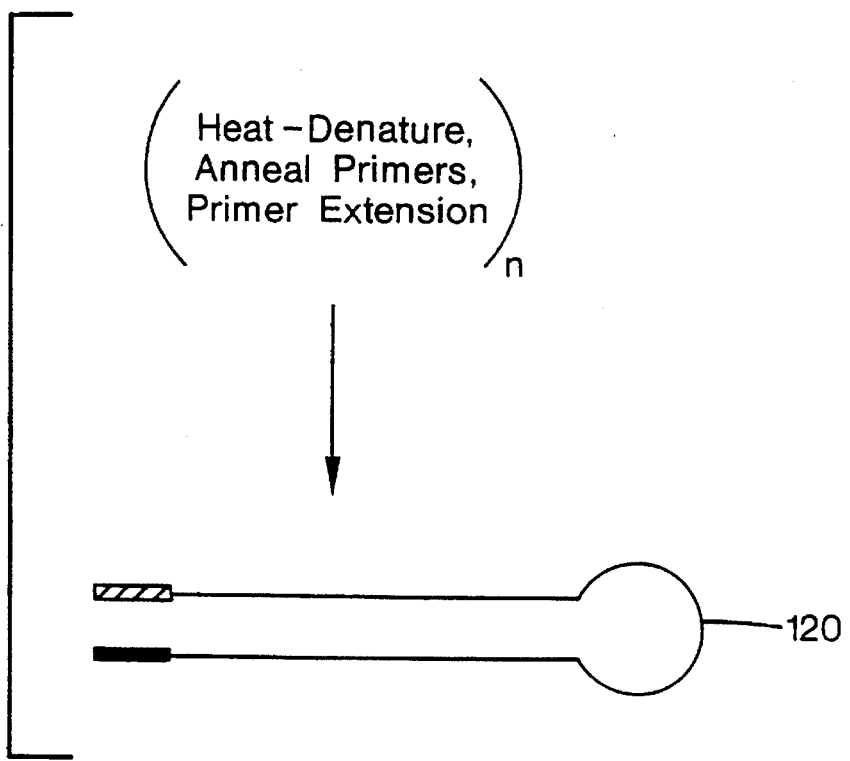
FIG. 3D is a continuation of FIG. 3C summarizing repeated cycles of DNA amplification in a BDA process using panhandled adapters and the type of DNA product formed therefrom.

Subsequent heat-denaturation of the duplex structures 112, 114 would signify the beginning of yet another BDA cycle. As shown in FIG. 3D, cycles as described above are repeated a sufficient number (n) of times until the desired amount of amplified DNA 120 is obtained. Generally, n is about 30 to 60 so as to achieve a satisfactory degree of amplification.

It will be appreciated by persons skilled in the art that at least one BDA cycle, such as a final one or more cycles, can be performed using one or more labeled dNTPs, thereby producing labeled BDA products.

When all cycles have been completed, DNA polymerase activity can be stopped by chilling the reaction mixture to about 4° C. or by adding EDTA to the reaction mixture to a concentration of about 10 mM.

After all the cycles of BDA are completed, samples of the amplified DNA can be loaded onto gels for analysis, using techniques well-known in the art. When working with new DNAs or when optimizing the BDA process for a particular application, cleaving the amplified DNA using one or more restriction endonucleases and looking for expected sizes of cleavage fragments in gels is a good way to confirm that the BDA was successful. Alternatively, one may choose to excise the amplified sequence of interest from the adapter using a restriction endonuclease and ligate the amplified sequence of interest into a cloning vector for sequence analysis.

Performing BDA using only one primer can result in amplification of either a portion of the SOI or the entire SOI, depending upon the location of the primer target site on the SOI.

Figure 4:
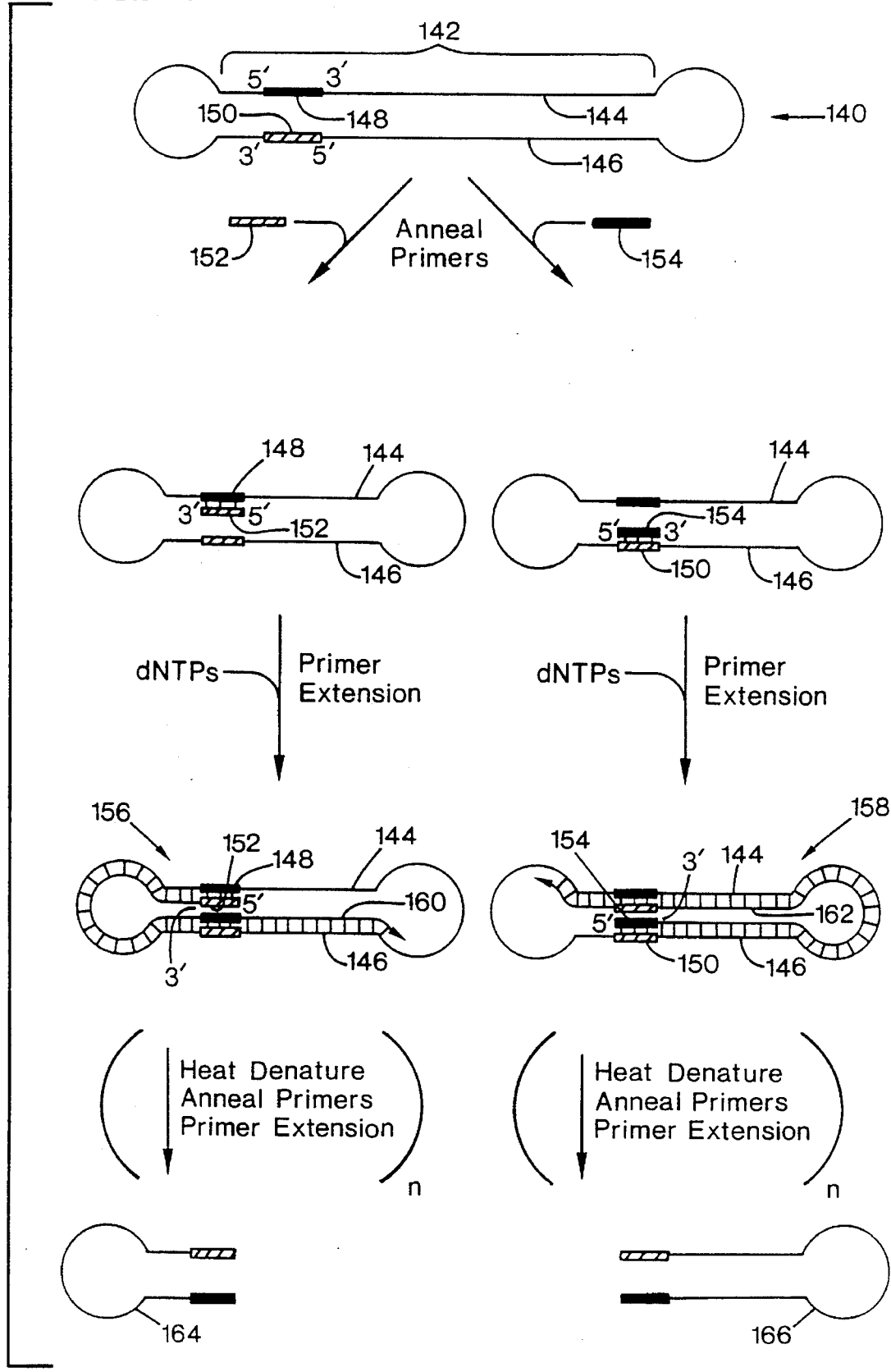
FIG. 4 schematically shows how a sequence of interest can be amplified using BDA and two non-homologous primers, thereby generating two different overlapping portions of the sequence of interest.

To this point, the descriptions of BDA have pertained to amplification of SOIs situated adjacent the primer target site. BDA also permits one to amplify an SOI that has a primer target site located completely within the SOI, such as when one wishes to amplify an entire genomic restrictions fragment. FIG. 4 schematically depicts how a BDA template 140, made using panhandled adapters, can be used to amplify an SOI 142, starting from a primer target site 148 located within the SOI 142. A similar reaction could be performed using double-stranded adapters, but the intermediate would not be a closed-loop structure.

Referring further to FIG. 4, the BDA template 140 is comprised of a first SOI region 144 and a second SOI region 146 complementary to the first SOI region.144. The first SOI region 144 includes a first primer target site 148; the second SOI region 146 includes a second primer target site 150 complementary to the first primer target site 148. BDA of such a template 140 can be performed using a first primer 152 complementary to the first primer target site 148 and a second primer 154 complementary to the second primer target site 150. Thus, the first and second primers 152, 154, respectively, are complementary to each other and are identical to primer target sites 150, 148, respectively.

Although FIG. 4 indicates that BDA involving the first primer 152 and the second primer 154 are performed in separate reactions, it is to be understood that BDA according to FIG. 4 can also be performed using both primers in a single reaction. However, such single-reaction BDA is not ideal because the primers 152, 154, being complementary to each other, can anneal to each other, thereby decreasing the efficiency of the BDA reaction.

Referring further to FIG. 4, a first BDA reaction mixture is prepared comprising the closed-loop structure 140, buffer, dNTPs, DNA polymerase, and required salts, as described above, and molecules of the first primer 152. A second BDA reaction mixture is prepared that is identical to the first reaction mixture except that the second primer 154 is added thereto instead of the first primer 152. The primers 152, 154 are allowed to anneal to the closed-loop structures 140. Subsequent primer extension (DNA synthesis) as described above yields the duplex structures 156, 158 comprising primer extension products 160, 162, respectively. Repeated-(n) cycles of heat denaturation, annealing of primers, and primer extension yield a large population of the structure 164 from the first BDA reaction and the structure 166 from the second BDA reaction. As can be seen, the BDA product 164 overlaps the BDA product 166 at the primer target sites. This overlap region can be effectively employed, should one desire, to unite the two products 164, 166 together into a single two-loop structure using molecular biological techniques known to skilled practitioners in the relevant art.

Figure 5A:
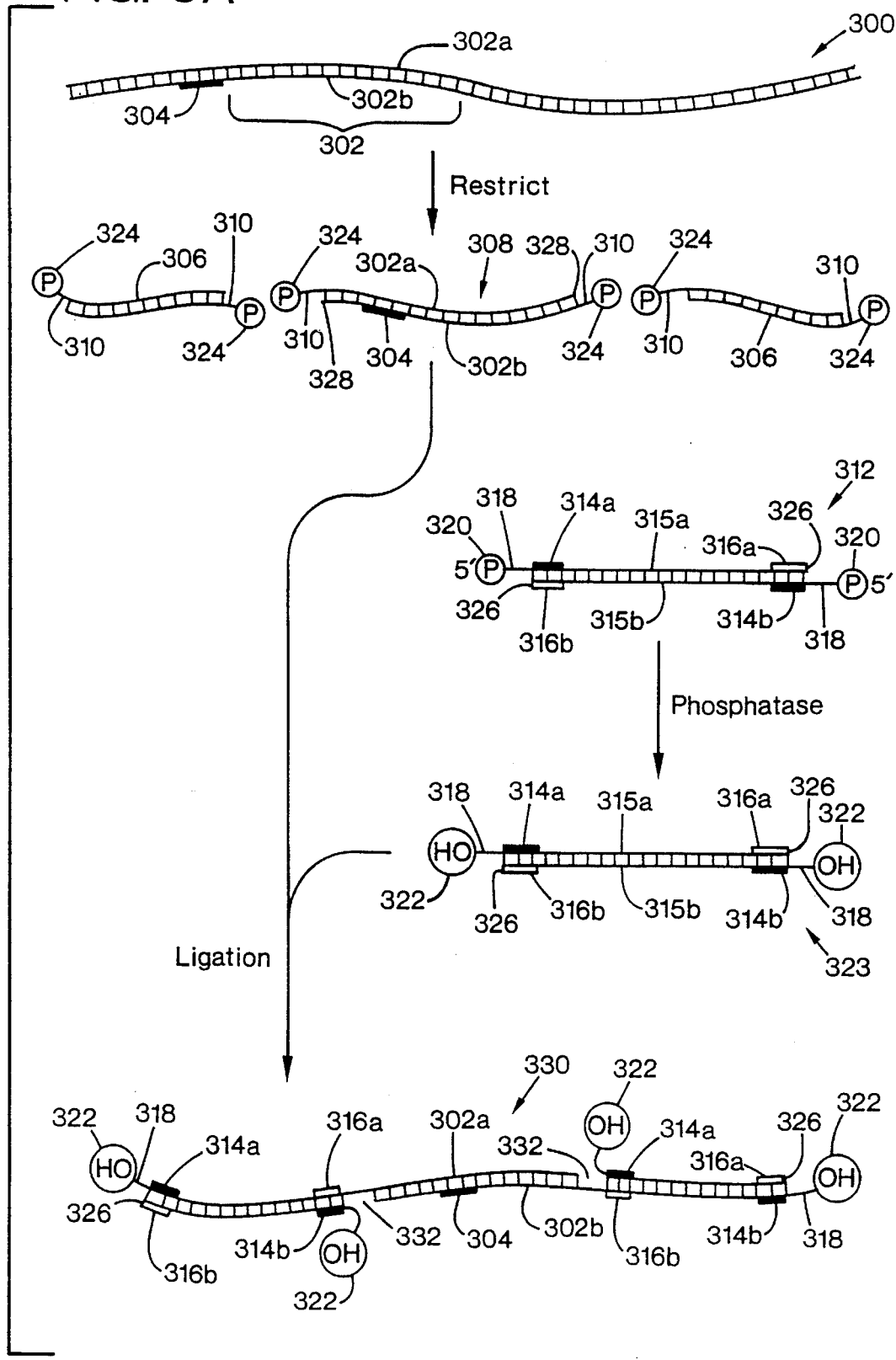
FIG. 5A schematically shows beginning steps in a BDA process according to the present invention, wherein sample DNA containing a sequence of interest is cleaved using a restriction endonuclease and double-stranded adapters are attached to the resulting fragments of sample DNA.

It is also possible to perform BDA using double-stranded adapters. Referring to FIG. 5A, a polynucleotide 300 contains an SOI 302 (comprised of segment 302a and complementary segment 302b) and a primer target site 304. Cleavage of the polynucleotide 300, such as by using a restriction endonuclease, generates a number of discrete fragments 306 that lack the primer target site, and fragments 308 that include the primer target site 304 and at least a portion of the SOI 302. Although each fragment 306, 308 preferably has "sticky" ends 310, the ends are in any event ligatable to adapters. (For clarity and simplicity of illustration, only the fragment 308 containing the primer target site 304 is shown and discussed further hereinbelow.)

The double-stranded adapters 312 have first self-complementary sequences 314a, 316a and second self-complementary sequences 314b, 316b. Thus, sequence 314b is identical to sequence 314a and sequence 316b is identical to sequence 316a. For optimal coupling to the fragments 306, 308, the adapters have ligatable ends 318. As shown in FIG. 5A, the ends 318 are preferably sticky to the sticky ends 310 of the fragments 306, 308. A spacer region 315a is situated between self-complementary sequences 314a and 316a, and a spacer region 315b, complementary to spacer region 315a, is situated between self-complementary sequences 314b and 316b.

It may be desirable, although not necessary in principle, to chemically alter the sticky ends 318 of the adapters 312 so that they are ligatable only to the ends of the fragments 306, 308 and not to each other. Thus, use of adapters with altered sticky ends can improve the efficiency of BDA performed using double-stranded adapters. One way to perform this alteration, as shown in FIG. 5A, is to treat the 5' ends of the adapters 312 with a phosphatase enzyme (such as calf-intestinal phosphatase or alkaline phosphatase) so as to remove the phosphate 320 normally present on said 5' ends (leaving a hydroxyl group 322 on treated adapters 323). Duplex DNAs treated in this manner are not ligatable to each other but can be ligated to untreated duplex DNAs such as the fragments 306, 308 having 5'-phosphates 324. That is, the hydroxyl group normally present on each 3' end 326 of either an untreated adapter 312 or a treated adapter 323 can be covalently coupled to a 5' phosphate 324. Thus, ligation of treated adapters 323 to fragments 308 can be achieved (albeit of only one strand because a hydroxyl normally present on each 3' end 328 of the fragments 308 cannot be ligated to a 5' hydroxyl 322 on a treated adapter 323). Treated adapters 323 cannot be ligated together because 5' hydroxyls 322 cannot be ligated to hydroxyls normally present on the 3' ends 326 of the adapters.

Ligation of a treated adapter 323 to each end of a fragment 308 produces a duplex structure 330 having unligated gaps 332. The gap 332 is formed because a 5' hydroxyl 322 does not couple to the hydroxyl normally present on each 3' end 328 of the fragment 308.

Figure 5B:
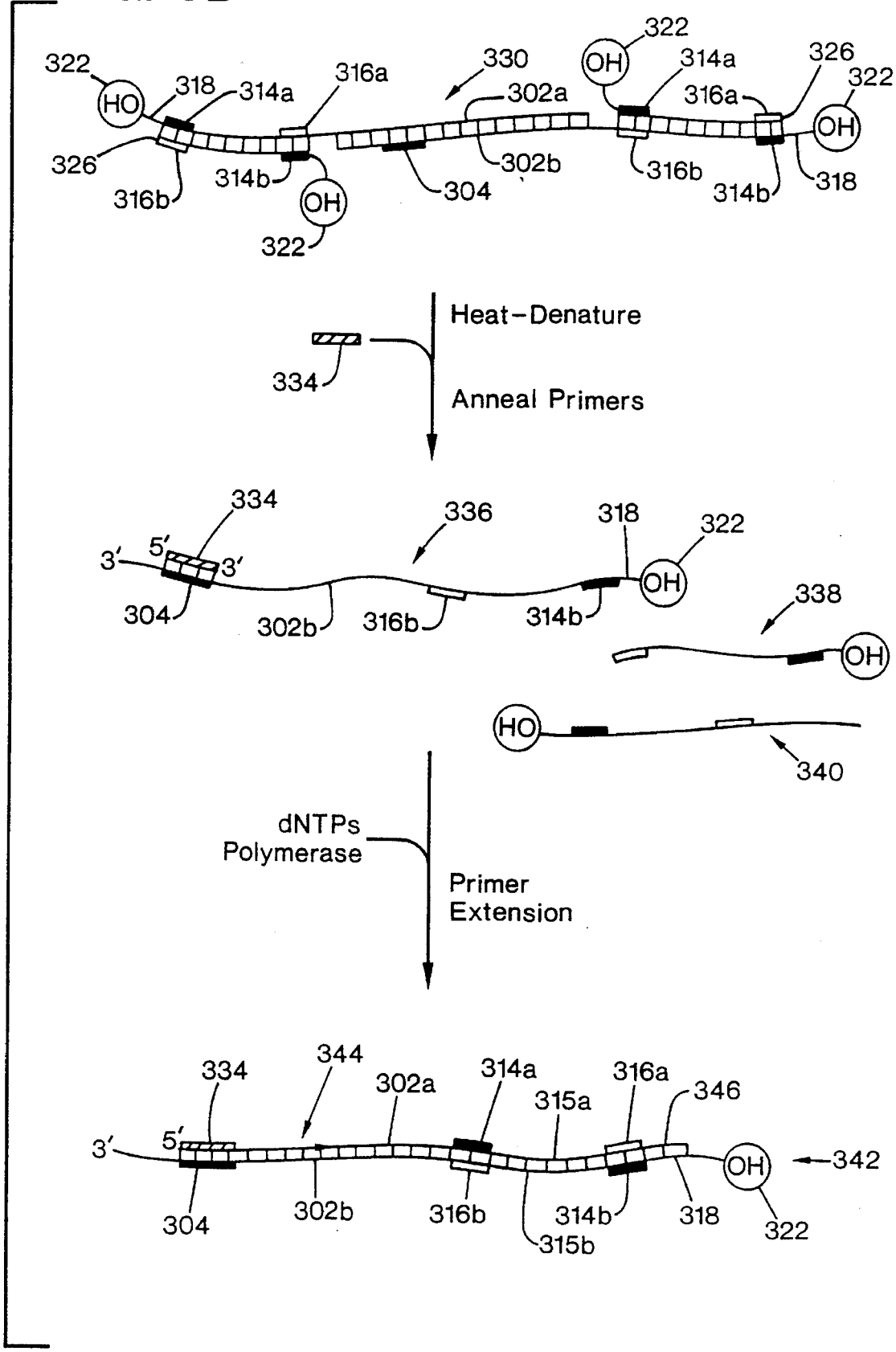
FIG. 5B is a continuation of FIG. 5A showing further steps in a BDA process employing double-stranded adapters.

Turning now to FIG. 5B, heat-denaturation of the duplex structures 330 followed by addition of oligonucleotide primers 334 substantially homologous to the primer target site 304 yields primed linear templates 336 and unprimed single-stranded molecules 338, 340. (The unprimed single-stranded molecules 338, 340 are not discussed further hereinbelow, even though it will be understood that the molecule 340 can form a duplex with itself which is extendable in a subsequent BDA cycle.) Primer extension of the linear template 336 produces a duplex molecule 342 that includes a primer extension product 344 which comprises a regenerated segment 302a of the SOI 302. The primer extension product 344 also includes the self-complementary sequence 314a, the spacer segment 315a, and an amount of the self-complementary sequence 316a sufficient to enable the primer extension product 344 to form a duplex with itself (via Watson-Crick pairing of bases in the self-complementary sequences 314a and 316a). Ideally, primer extension continues through the self-complementary sequence 316a to include a short segment 346 complementary to the sticky end 318. Of course, if the adapters 312 had blunt ends, the short segment 346 would not be formed.

Figure 5C:
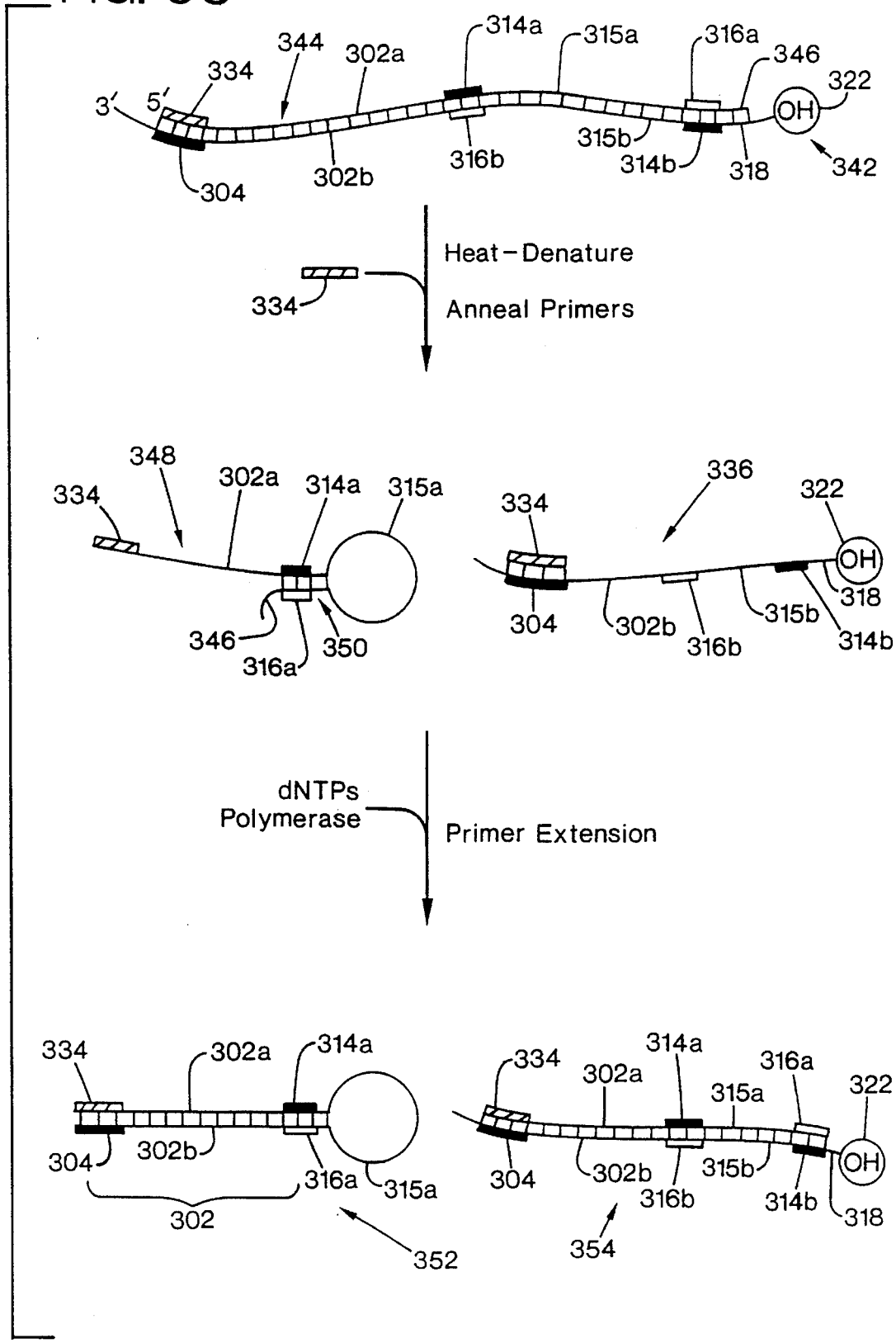
FIG. 5C is a continuation of FIG. 5B showing further steps in a BDA process employing double-stranded adapters.

Referring to FIG. 5C, heat denaturation of the duplex molecule 342 and annealing of primers 334 reproduces the primed template 336 and produces a looped template 348 from the primer extension product 344. The looped template 348 includes a duplex region 350 formed by the annealing together of self-complementary sequences 314a and 316a. The spacer 315a thus becomes a loop. The short segment 346, if present in the duplex 342, is preserved in the looped template 348.

Continuing with FIG. 5C, primer extension of the templates 348, 336 yields the duplexes 352, 354, respectively. Use of a DNA polymerase such as Vent™ polymerase (which has a 3'-exonuclease function) removes the unpaired segment 346. Thus, as can be seen, in the looped template 348, the self-complementary sequence 316a serves as a primer for the regeneration of segment 302b and the primer target site 304. As can be seen, the duplex 354 is structurally similar to the duplex 342 formed earlier (FIG. 5B). The duplex 352 is structurally similar to the BDA product 120 of FIG. 3D. Subsequent cycles of BDA result in amplification of the duplex 352, which comprises the SOI 302, as well as production of more molecules of the duplexes 352 and 354.

Thus, BDA allows researchers to clone entire genomic restriction fragments with a knowledge of the sequence of only one priming region in the restriction fragment. In addition, a portion of a DNA sequence amplified by BDA can be used as a primer for subsequent BDA reactions on templates made with adapters ligated to DNAs cut with a different restriction enzyme. This would effectively enable one to "walk" along genomic DNAs one restriction fragment at a time and determine the sequence of or clone each fragment.

BDA differs from existing PCR methods in two important aspects. First, BDA is not limited to amplifying the region located between two priming sites. Because of its inability to amplify sequences lying outside two priming sites, PCR is most commonly employed only as an aid in cloning gene sequences located between priming sites. For example, PCR can be used to amplify a section of a gene useful for making a radioactive probe. Such probes are useful for isolating clones containing an entire gene from genomic (or cDNA) libraries. But, making such libraries and probing them with PCR-generated probes can be exceedingly time-intensive, often taking months to obtain entire genes. BDA, on the other hand, which can produce amplified entire restriction fragments from a single priming region, can amplify an entire gene in a single overnight reaction after selection of the appropriate restriction fragment.

A second primary advantage of BDA is its ability to allow users to "walk" along a genomic DNA and determine its entire sequence by employing multiple "rounds" of BDA and DNA sequencing. In such a scheme, each preceding round yields information utilized in the subsequent round. Briefly, the BDA portion of each "round" is comprised of multiple BDA cycles as described above. A first round is begun by cutting the genomic DNA using a first restriction endonuclease. The resulting population of linear duplex DNA fragments includes a group of substantially identical fragments to be sequenced which include a first primer target site, a first region (to be sequenced) and an opposing second region complementary to the first region. To prepare the fragments for BDA, suitable adapter molecules as described generally above are ligated thereto. The adapters, of course, have ends ligatable to the fragments. The resulting templates are denatured. Primers homologous to the first primer target site are annealed to the denatured templates. The primers are then extended as described above, forming primer extension products. After denaturing the primer extension products from the templates, further BDA cycles are performed, as described above, until sufficient DNA is produced to permit conventional sequencing of the amplified DNA to be performed. After sequencing, a second round is initiated by selecting a new primer target site situated within the sequence obtained in the first round, but downstream of the first primer target site (thereby ensuring that DNA amplified in the second round will overlap DNA amplified in the first round). The genomic DNA is then cut using a second restriction endonuclease. Using new primers homologous to the second primer target site, multiple cycles of BDA are performed, as described above, yielding DNA amplified sufficiently to permit sequencing. By registering the sequence information determined in the first round with sequence information determined in the second round, the combined sequence of the DNA amplified in both rounds is obtained. Further rounds could, in theory, be performed in each direction until a complete genomic segment such as a chromosome has been sequenced.

This "walking" feature is extremely useful for sequencing and/or cloning very large genetic sequences spanning many restriction fragments. Very large genes, such as those extending across multiple restriction fragments, are oftentimes very difficult to clone using genomic libraries and conventional methods due to the limited capacity of most vectors to carry large sequences. In these cases, BDA may be the only means of obtaining complete large gene sequences, particularly without spending large amounts of time. This "walking" ability of BDA should prove extremely useful in projects involving genomic sequencing, such as the human genome effort or similar efforts proposed for commercially important crops or livestock.

Figure 6:
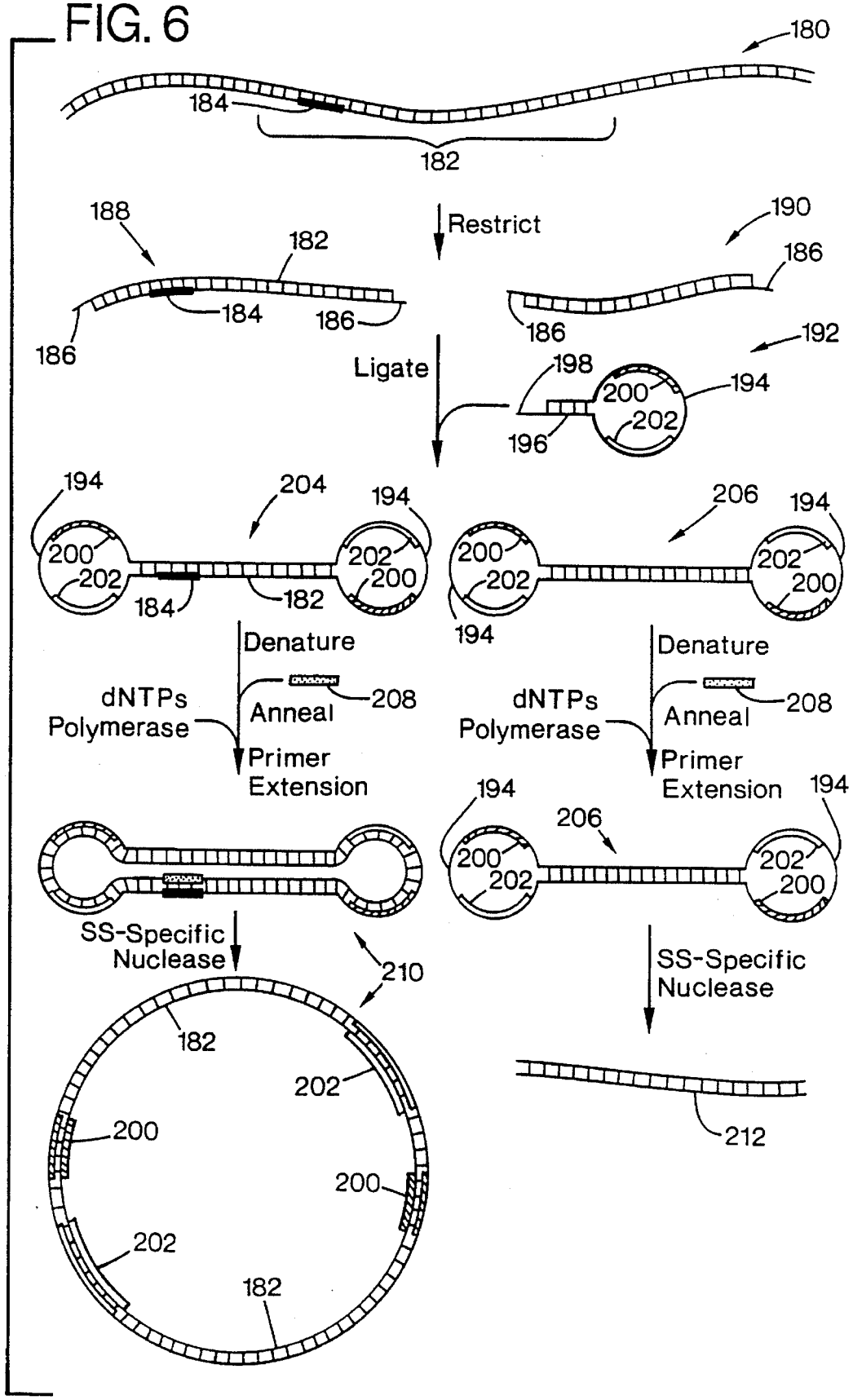
FIG. 6 schematically illustrates a method by which BDA can be used to produce a clonable vector of a sequence of interest without the need to perform repeated cycles of DNA replication.

BDA can also be used to selectively clone an SOI, thereby ultimately achieving a de facto amplification of the SOI without the need for performing multiple cycles of annealing, primer extension, and denaturation. An example of a BDA cloning method is as follows:

Referring to FIG. 6, genomic or other DNA 180 containing one or more copies of an SOI 182 (including a primer target site 184) is cleaved using a restriction endonuclease. The particular restriction endonuclease used is chosen to ensure that the cleavage products therefrom have a desired "sticky end" 186. Of the population of cleavage products so generated, a first subpopulation 188 will include the SOI 182 and a second subpopulation 190 will not.

BDA adapters 192 are then added to the cleavage products. The BDA adapters have the same "panhandle" configuration as described above, including a single-stranded spacer 194, a duplex region 196, and a sticky end 198. The sticky end 198 is complementary to the sticky ends 186 on the cleavage products 188, 190. The duplex region 196 is an inverted repeat, as described above. The single-stranded spacer 194 includes a replication origin 200 expressible in a cloning host cell such as E. coli. The spacer 194 also includes a selectable marker 202, such as a gene conferring resistance to an antibiotic. (FIG. 6 and the above description depict the replication origin 200 and selectable marker 202 as being located in the spacer 194. However, there is no reason per se why the replication origin 200 and selectable marker 202 could not be situated either partially or wholly within the duplex region 196.) Thus, the adapters 192 used for BDA cloning will typically be larger than adapters used for BDA alone.

The mixture of adapters 192 and cleavage products 188, 190 are ligated together as described above, thereby generating closed-loop structures 204, 206.

Primers 208 homologous to the primer target site 184 in the SOI 182 (and therefore specific for the SOI) are added to the closed-loop structures 204, 206. All four dNTPs and a suitable DNA polymerase, as described above, are also added. The amount of dNTPs and DNA polymerase added are sufficient for a single BDA cycle. The resulting mixture is heat-denatured, then cooled to allow the primers 208 to anneal to the primer target sites 184. Of course, closed-loop structures 206 lacking the SOI (and therefore the primer target site) will not experience any significant binding of primers thereto.

Subsequent DNA replication (primer extension) is allowed to proceed for a time sufficient for the DNA polymerase molecules to fully circumnavigate the closed-loop structure 204 containing the SOI 182. Such a time would normally be slightly longer than the time, as described above, that would allowed for a DNA polymerase to at least travel past the region on the SOI complementary to the primer target site 184. Thus, the closed-loop structure 204 containing the SOI 182 will become fully replicated, thereby generating circular duplexes 210 that include the SOI 182, the replication origin 200, and the selectable marker 202. The closed-loop structures 206 lacking the SOI 182 are not replicated. Thus, the closed-loop structures 206 lacking the SOI 182 (and therefore lacking the primer target site) retain their single-stranded loop portions after DNA replication.

After DNA replication, the reaction mixture is treated with a single-strand-specific nuclease (a nuclease that specifically degrades single-stranded DNA). Representative nucleases for this purpose include, but are not necessarily limited to, Mung Bean nuclease and S1 nuclease. If S1 nuclease is to be used, it is desirable to treat the replication mixture with a DNA ligase to convert the gapped structure 210 produced by primed DNA replication into a fully-covalently closed circular duplex. This is because S1 will nick gapped duplexes. Mung Bean nuclease, however, will not nick gapped duplexes and no such ligase treatment is necessary. The single-stranded portions of all DNAs (in particular, closed-loop structures 206 lacking the SOI) are degraded, leaving only a linear duplex 212 lacking the replication origin and selectable marker. The circular duplex DNAs 210 are not degraded.

After nuclease treatment, the DNA mixture is transformed into cells of a susceptible host such as E. coli. The resulting transformed cells are cultured under conditions favoring survival of cells that received the fully duplex DNA, such as by culturing in the presence of the antibiotic corresponding to the antibiotic resistance marker 202. Transformed cells that receive only a linear duplex 212 lacking the replication origin and selectable marker do not survive. Transformed cells that receive a circular duplex 210 including the replication origin 200 and selectable marker 202 do survive, enabling large amounts of the SOI to be produced by continued selective culturing of the cells.

In order to further illustrate the invention, the following examples are given.

EXAMPLE 1

This example pertains to the synthesis of a plasmid, pIR8, useful for preparing "panhandle" adapter molecules. pIR8 is only one example of a suitable plasmid for making adapters. It will be appreciated by persons skilled in the art that other plasmids can be employed using similar methodology. It will also be appreciated that suitable adapters can be produced using automated nucleotide synthesizer technology known in the art.

The pIR8 plasmid was constructed by first cutting a pUC19 plasmid cloning vector (Yanisch-Perron et al., Gene 33:103[14] 119 (1985); ATCC Accession No. 37254; 2686 base pairs in length) at its unique NarI and EcoRI sites. (NarI cuts pUC19 at nucleotide 235 and EcoRI cuts at nucleotide 396.) The resulting restriction fragments were blunted using the Klenow fragment of *E. coli* DNA polymerase I plus all four dNTPs, and ligated using T4 DNA ligase. This created a molecule "BDA I" which had a regenerated EcoRI site at the former NarI site. BDA I includes all the nucleotides of pUC19 except nucleotides 235–396. It also contains the polylinker cloning site of pUC19 having the following sequence (Seq. ID NO.:1):

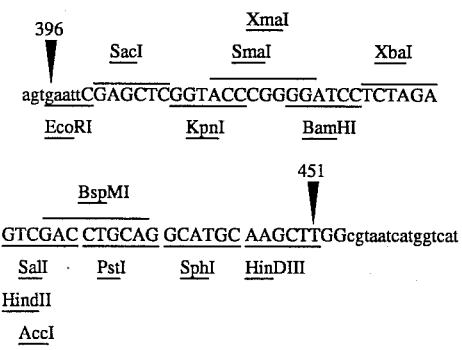

wherein restriction enzyme cleavage sites are indicated. The polylinker cloning site spans from nucleotide 396 to nucleotide 451.

BDA I was cut at its unique HinDIII and ScaI sites. (HinDIII cuts pUC19 at nucleotide 447 and ScaI cuts at nucleotide 2177.) The two resulting fragments were blunted using the Klenow fragment of DNA polymerase I and all four dNTPs. The smaller fragment thus generated was separated from the larger fragment by electrophoresis in low-melt agarose. Similarly, a pUC18 plasmid (Yanisch-Perron et al., id.), which differs from pUC19 only in having its polylinker cloning site oriented in reverse, was cut at its unique NarI and ScaI sites. The two resulting fragments were blunted using the Klenow fragment and all four dNTPs. The larger fragment was purified by electrophoresis in low-melt agarose. The larger fragment of pUC18 and the smaller fragment of BDA I thus prepared were ligated together using T4 DNA ligase and subsequently transformed into *E. coli*. Selection on Amp plates yielded transformants containing a recombinant plasmid pIR8.

Figure 7:
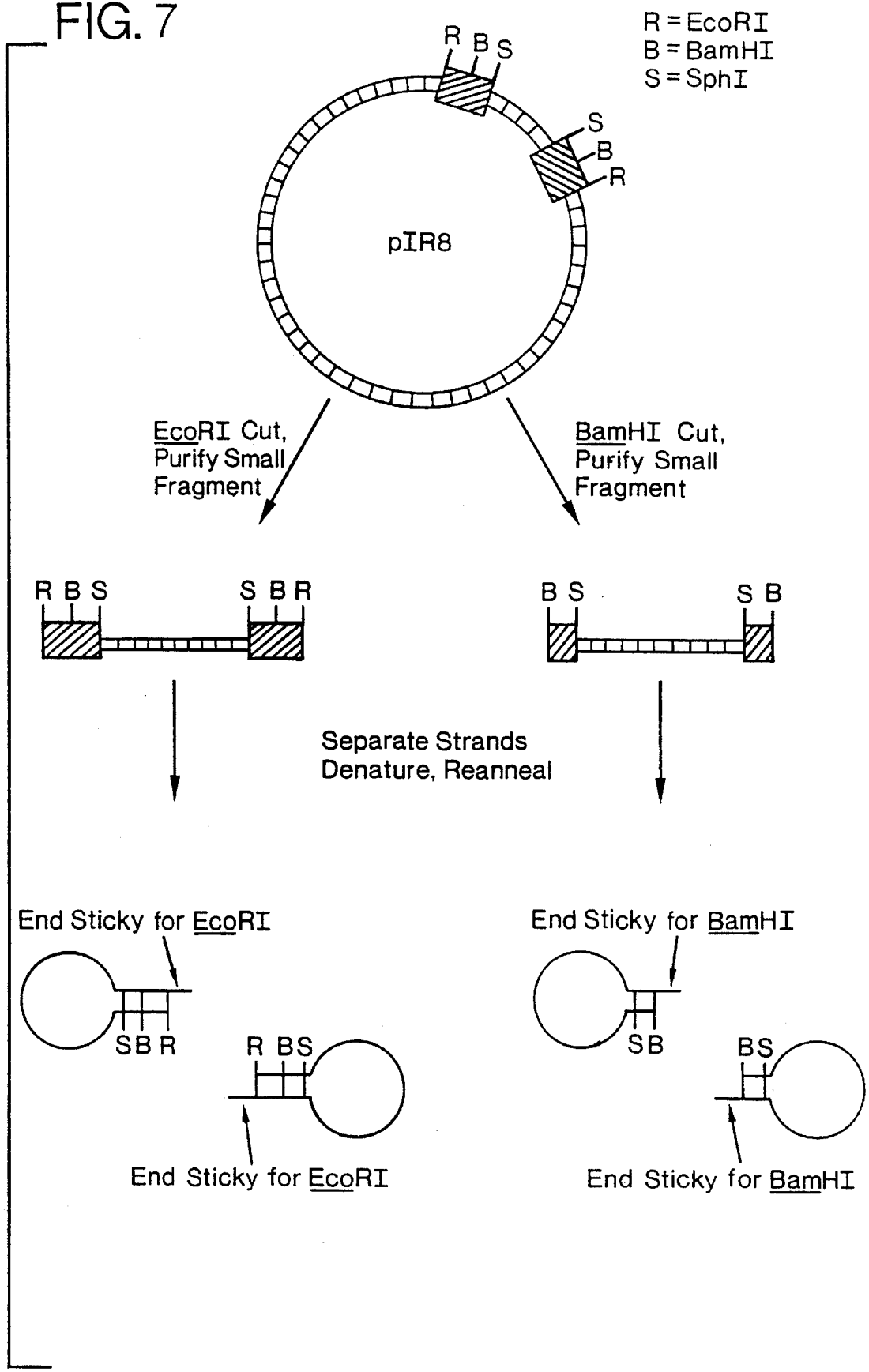
FIG. 7 schematically illustrates the production of BDA adapters from a recombinant plasmid, pIR8, as described in Example 1.

The pIR8 plasmid has the polylinkers of pUC18 and pUC19 placed in an inverted orientation relative to each other. As shown in FIG. 7, cutting pIR8 with any of the restriction enzymes that cut within the polylinker (except HinDIII) generates a large fragment and a small fragment each with identical ends. For better efficiency in the cycling reactions, the smaller molecules are preferred for use as adapters in BDA. As detailed elsewhere herein, the larger fragment is useful for a non-cycling BDA reaction because it contains both a replication origin for *E. coli* and a selectable marker. Due to the inverted orientation of the polylinkers, inverted repeats capable of pairing within the single strands of the small fragment range from 11 bases (SphI-cut) to 60 bases (EcoRI-cut).

The adapters were purified by cloning a fragment containing the self-complementary polylinker sequences of pIR8 into phagemid DNA with subsequent generation of single strands using M13-derived phage, restriction-enzyme digestion, and isolation on acrylamide gels. The protocol was as follows:

The small EcoRI fragment of pIR8 was ligated into the unique EcoRI site of a pIB plasmid to create the plasmid pMIR1. The pIB plasmid was constructed by: (a) cutting the commercially available phagemid pIB130 (available from International Biotechnologies, Inc., New Haven, Conn.) with SacI and HinDIII; (b) blunting the ends of the fragments using the Klenow fragment and all four dNTPs; and (c) ligating with T4 DNA ligase. The pMIR1 DNA was transformed into MV1190 cells (containing the F pilus) which were subsequently allowed to grow to early log phase and then superinfected with the M13-based vector designated M13KO7 (available from International Biotechnologies, Inc., New Haven, Conn.). The mixture was allowed to shake for 45 minutes at 37° C. Kanamycin was added to select for cells containing both the M13KO7 and pMIR1 plasmids. After 16 hours, single-stranded DNA was purified from the cells. In this DNA, the ratio of pMIR1 DNA to M13KO7 DNA was about ten to one. This DNA mixture was heated to 75° C. in BamHI buffer (150 mM NaCl, 10 mM Tris-HCl pH 7.9, 10 mM $MgCl_2$, 1 mM dithiothreitol, 100 μg/mL BSA) and allowed to cool slowly to 37° C. to allow the inverted polylinker sequences in pMIR1 to self-anneal. Three units of BamHI were added per microgram of pMIR1 DNA and the resulting 224-base adapter molecule was purified from 5% acrylamide gels. Approximately 5 μg of adapter (as determined via fluorescence with ethidium bromide) was recovered in this manner. The concentration of the adapter was about 105 ng/μL.

EXAMPLE 2

An adapter molecule suitable for BDA was synthesized chemically. The sequence of the entire 121-nucleotide molecule (there is no complementary strand) was as follows Seq. ID NO.:2):

5'GATCCCGGGTACCATGGCCAAGCTTAAGTACTCGCTTTTG

```
GGTTAGGAGAGCAGCATCTGACGACGGAGATGACGGAAAT
GAAAACGACGGCGAGTACTTAAGCTTGGCCATGGTACCCGG3'
```

Significant features of this molecule include a duplex of 31 base-pairs with unique recognition sites for XmaI (SmaI), KpnI, NcoI, EaeI, MscI, HindIII, AflII, and ScaI; an overhanging 5' end sticky for BamHI, BglII, MboI, or BclI; and a 54-base singly-stranded loop sequence.

EXAMPLE 3

A 341-bp Sau3A I duplex fragment from pUC18 (spanning nucleotides 1662 to 2003) was purified from low-melt agarose for use as a template usable for BDA (sequence containing an SOI).

The sequence (Seq. ID NO.:3) of one of the strands of the fragment is as follows (complementary strand not shown):

```
5'gatctgtctatttcgttcatccatagttgcctgactccccgtcgtgtaga
taactacgatacgggagggcttaccatctggccccagtgctgcaatgata
ccgcgagacccacgctcaccggctccagatttatcagcaataaaccagcc
agccggaagggccgagcgcagaagtggtcctgcaactttatccgcctcca
tccagtctattaattattaccagaaagctagagtaagtagttcgccagtt
aatagtttgcgcaacgttgttgccattgctacaggcatcgtggtgtcacg
ctcgtcgtttggtatggcttcattcagctccggttcccaac3'
``` wherein a 5-base diagnostic restriction site for AvaII is underlined. Also, a 21-base primer target site and a 30-base primer target site are underlined. The initial gate, of course, represents an overhanging sticky end.

The ends of this fragment were "sticky" to the ends of the 224-base BamHI-cut adapter of Example 1. Concentration of the 341-bp fragment was determined by fluorescence in the presence of ethidium bromide to be 200 ng per μL.

EXAMPLES 4–10

An important step in BDA is ligation of adapters to the templates. Too few adapters present during ligation will lead to increased ligation of templates to each other rather than to adapters.

Three ligation products were prepared utilizing 0.2 pg (Ligation A), 2 pg (Ligation B), and 20 pg (Ligation C) of the 341-bp template of Example 3, each in the presence of 0.2 μg of the adapter of Example 1, wherein 0.2 pg of 341-bp template corresponds to about 535,000 copies thereof. Ligation reactions were performed at 16° C. in 20 μL volume of 1×T4 ligase buffer (50 mM Tris-HCl pH 7.8, 10 mM MgCl$_2$, 20 mM DTT, 1 mM ATP, 50 μg/mL BSA) and 400 units of T4 DNA ligase from New England BioLabs, Beverly, Mass. The molar ratios of adapter to 341-bp template in Ligations A, B, and C were 3,000,000 to 1, 300,000 to 1, and 30,000 to 1, respectively. No extraneous DNA (i.e., no non-target DNA) was included in these ligations to minimize effects arising from non-specific priming of replication. The ligation reaction conditions were chosen with two aims: (1) to maximize likelihood of ligating the 341-bp template to the adapters using high molar ratios of adapter to template; and (2) to mimic the amount of DNA typically used in a ligation reaction (wherein 0.2 μg=2.6 μM of 5' ends).

Another variable to be controlled in BDA is the concentration of primer because, unlike with PCR, complementary strands are held in close proximity, even after denaturation. This is due to the "closed loop" structure of the starting substrates and the fold-back structure of the replication products made in subsequent cycles of replication.

A 30-base primer (5'AACTACTTACTCTAGCTTCCCG-GCAACAAT3') was synthesized. This sequence (Seq. ID NO.:4) is complementary to the region from nucleotide 1903 to nucleotide 1874 of pUC18 within the 341-bp template of Example 3. This is exactly 100 bases from one end of the template. Thus, extension of the primer from the 3' end thereof would yield a complementary 241-bp sequence (including the primer).

Seven different BDA reactions were set up using the ligation products as described above and various molar ratios of primers relative to the corresponding ligation product. (Normally, PCR utilizes 25 pmol primer to 456,000 copies of template (or $3.3 \times 10^7$ primers relative per template)). Examples, with corresponding amounts of primers and ligation products, are tabulated below:

| Ex. | # primers | # target segs. | primer/ target | ligation product |
|---|---|---|---|---|
| 4 | $1.65 \times 10^{13}$ | $5.35 \times 10^5$ | $3.08 \times 10^7$ | A |
| 5 | $1.65 \times 10^{14}$ | $5.35 \times 10^5$ | $3.08 \times 10^8$ | B |
| 6 | $1.65 \times 10^{15}$ | $5.35 \times 10^5$ | $3.08 \times 10^9$ | B |
| 7 | $1.34 \times 10^{14}$ | $4.28 \times 10^6$ | $3.13 \times 10^7$ | B |
| 8 | $1.65 \times 10^{15}$ | $5.08 \times 10^7$ | $3.25 \times 10^7$ | C |
| 9 | $1.65 \times 10^{13}$ | $5.35 \times 10^5$ | $3.08 \times 10^7$ | C |
| 10 | $1.65 \times 10^{14}$ | $5.35 \times 10^5$ | $3.08 \times 10^8$ | C |

Examples 4, 5, 6, 7, and 8 were all performed using Vent™ DNA Polymerase (from New England BioLabs, Beverly, Mass.), using the manufacturer's recommended reaction conditions (10 mM KCl, 20 mM Tris-HCl pH 8.8 at 25° C., 10 mM ammonium sulfate, 2 mM magnesium sulfate, 0.1% Triton X-100, 100 μg/mL BSA, 200 μM of each dNTP, 10 units of enzyme) in 100 μL volumes under mineral oil. Examples 9 and 10 were performed using about two Units of Taq DNA Polymerase (from Promega Biotec, Madison, Wis.) and according to the manufacturer's recommended conditions in 100 μL volumes under mineral oil. All BDA reaction mixtures were prepared on ice prior to initiation of the reactions on a Perkin-Elmer-Cetus PCR machine. BDA cycles were defined as follows:

1. Heat to 96° C. Hold 5 minutes.
2. Cool to 55° C. Hold for 1 minute.
3. Heat to 72° C. Hold for 45 seconds.
4. Heat to 96° C. Hold for 1 minute.
5. Repeat steps 2–4 for a total of 45 cycles.
6. On the last cycle, the 72° C. reaction was incubated for 2 minutes rather than 45 seconds and was not subsequently heated to 96° C. Afterward, the reactions were cooled to 10° C. for storage until analysis.

All of Examples 4–10 were simultaneously treated under the above conditions. Upon completion of the BDA, the reaction mixtures were extracted with chloroform to remove the mineral oil and 15 μL from each Example were electrophoresed on a 5% acrylamide gel stained with ethidium bromide. (Whenever a band resulting from a BDA reaction is evident on a gel stained with ethidium bromide, it is an indication that DNA replication occurred in the corresponding BDA reaction. This is because there is an insufficient amount of starting DNA in any of the reactions to produce any bands on the gel.) Example 4, 5, 7 and 8 produced multiple bands in the range of 500 base pairs (bp) to 1 kilobase pairs (kbp). Example 8 produced a single band of about 700 bp. The predicted length of a full duplex arising from BDA amplification of the 341 bp fragment is 713 bp. (The presence of single-stranded loops in any BDA-produced molecule adds a degree of uncertainty in predicting molecular sizes. Such loops are understood by persons skilled in the art to exhibit anomalous migration behavior in gels.) Examples 4, 5, and 7 also exhibited faint bands of about 700 bp as well as other bands.

To more accurately characterize the structure of these BDA products, the reaction of each Example was first eluted through Centricon 100 filters (available from Amicon, Beverly, Mass.) to separate low molecular-weight compounds such as buffer and primers from the BDA products. One-third of the eluted volume of each Example was either digested with SalI or left uncut as a control. SalI cleaves within the polylinker of the adapter and was expected to release the replicated template portion of the BDA product from the adapter portion. Thus, SalI digestion of full-duplex (b) Template concentration (relative to adapter concentration) can be varied to some extent in the ligation of adapters to templates and still result in BDA products. Even though the exact composition of the BDA products produced in Examples 4–10 was not clear from the limited analyses performed, these Examples did provide ranges for certain BDA reaction conditions that were useful in subsequent Examples; and (c) Some non-specific priming occurred in these reactions, probably as a result of high primer concentration, thereby generating certain artifacts. Such binding would give rise to artificially high amounts of adapter DNA. Raising the annealing temperature or incorporating trimethyl ammonium chloride into the reaction would be expected to ameliorate these problems.

EXAMPLE 11

An adapter (Seq. ID NO.:5) was synthesized having the following sequence (wherein the polylinker regions are indicated by capital letters):

| 267-base EcoRI-cut Adapter: |
| --- |
| 5'GAATTCGAGCTCGGTACCCGGGGATCCTCTAGAGTCGACCTGCAGGCATG<br>CAAGCTcgccattcgccattcaggctgcgcaactgttgggaagggcgaatc<br>ggtgcgggcctcttcgctattacgccagctggcgaaaggggatgtgctg<br>caaggcgattaagttgggtaacgccagggttttcccagtcacgacgttgt<br>aaaacgacggccagtaAGCTTGCATGCCTGCAGGTCGTCTCTAGAGGATC<br>CCCGGGTACCGAGCTCG3' | was expected to produce molecular fragment sizes of about 254 bp (template portion) and about 205 bp (adapter portion). SalI digestion of looped-duplex BDA products was expected to produce fragment sizes of about 254 bp (template portion) and a fragment of indeterminate length probably having an apparent size of about 330 bp due to the presence of the looped adapter.

SalI digestion of Example 4 yielded a prominent band at about 205 bp, a less intense band at 225 bp, a faint band near 250 bp, another faint band near 290 bp, a moderately intense band near 330 bp, several faint bands of less than 150 bp, and several bands between 500 bp and 1 kbp that appeared to be uncut. SalI digestion of Example 5 yielded a quantity of uncut DNAs between 500 pb and 1 kbp, a band near 330 bp, and a band near 290 bp. SalI digestion of Example 7 yielded results very similar to SalI-cut Example 5. SalI digestion of Example 8 exhibited very faint bands near 330 bp and possibly 210 bp.

These data indicate that:

(a) BDA reaction conditions utilizing about 2 pg of template DNA produce detectable BDA products;

A 6-base diagnostic restriction site for PvuII is underlined. Also, a 4-base restriction site for Sau3A is underlined.

Although not used in any of the Examples disclosed herein, this adapter is useful for BDA.

EXAMPLE 12

An adapter (Seq. ID NO.:6) was synthesized having the following sequence (wherein the polylinker regions are indicated by capital letters):

| 224-base BamHI-cut Adapter: |
| --- |
| 5'GATCCTCTAGAGTCGACCTGCAGGCATGCAAGCTcgccattcgccattca<br>ggctgcgcaactgttgggaagggcgatcggtgcgggcctcttcgctatta<br>cgccagctggcgaaaggggatgtgctgcaaggcgattaagttgggtaac<br>gccagggttttcccagtcacgacgttgtaaaacgacggccagtaAGCTTG<br>CATGCCTGCAGGTCGTCTCTAGAG3' |

A 6-base diagnostic restriction site for PvuII is underlined. Also, a 4-base restriction site for SaU3A is underlined.

EXAMPLE 13

The following primers were synthesized: a 30-base primer having the sequence (Seq. ID NO.:7):

5'aactacttactctagcttcccggcaacaat3' and a 21-base primer having the sequence (Seq. ID NO.:8):

5'gatctgtctatttcgttcatc3'.

When these primers are used together in a PCR reaction with the template of Example 3, the product is a 241-bp sequence that serves as an internal control. Production of this 241-bp fragment indicates that conditions are appropriate for PCR to occur.

EXAMPLES 14–23

These Examples comprise experiments that were performed to examine the contribution to a BDA reaction of each of the components thereof. These Examples utilized standard conditions for BDA, annealing, elongation, and denaturation, as outlined below.

At time of use, BDA samples were extracted once with 120 μL of chloroform/isoamyl alcohol (24/1). 15 μL of each sample were electrophoresed in gels for size analysis using standard methods.

Ligations for all BDA reactions were as follows: 0.2 μg of the adapter of Example 12 cut with BamHI was ligated to 200 pg of Sau3A-digested DNA. Ligation of DNA was assayed by production of dimers of the Example-12 Adapter. Typically, the template to be amplified was the 341-bp Sau3A I fragment of Example 3. However, Arabidopsis genomic DNA was used where indicated. In all ligations, the same amount of T4 DNA ligase was used as described in Examples 4–10. The same ligation conditions were used throughout.

All BDA and PCR reactions, unless noted otherwise, utilized 2 pg of template DNA, 2 μg of 21-base primer (Example 13), and/or 2.7 μg of 30-base primer (Example 13). Reactions were performed using either the Vent™ DNA polymerase (obtained from New England BioLabs, Beverly, Mass.) or Taq DNA polymerase (obtained from Promega, Madison, Wis.) according to manufacturer's specifications. No apparent difference was noted in substrate specificity or amount of product produced by either enzyme.

PCR reactions were performed using conventional protocol.

The BDA reaction cycle profile was as follows:
1. Heat to 96° C. for 5 minutes.
2. Cool to 58° C. for 2 minutes.
3. Heat to 72° C. for 45 seconds.
4. Heat to 96° C. for 1 minute.
5. Cool to 58° C. for 20 seconds.
6. Repeat steps 3–5 45 times.
7. Heat to 96° C. for 1 minute.
8. Cool to 58° C. for 20 seconds.
9. Heat to 72° C. for 2 minutes.
10. Store at 10° C. overnight or until use.

When restriction mapping was performed, the BDA samples were purified by centrifugation on Centricon 100 filters and eluted with three 1-mL washings of water to remove small impurities and primers. Restriction analysis utilized 15 μL of each sample and 4 to 5 Units of each corresponding restriction endonuclease.

Specifically, each Example was performed, and results obtained, as follows:

Example 14: A standard PCR reaction performed using the template of Example 3 and the 30-base and 21-base primers of Example 13. A strong 241-bp band was produced. This indicated that PCR works using this template and these primers under the conditions employed below for BDA.

Example 15: BDA was attempted using a non-ligated mixture of the Example-12 adapter, the Example-3 template, and the 21-base primer of Example 13. No BDA products were evident on the gel, indicating that ligation of adapters to the template is essential for BDA.

Example 16: BDA was attempted using a ligated mixture of the Example-3 template and 0.2 μg of Sau3A I-digested Arabidopsis genomic DNA (instead of the Example-12 Adapter). The 30-base primer of Example 13 was used. No BDA products were evident on the gel, indicating that a looped adapter is essential for BDA.

Example 17: As in Example 16 except that the 21-base primer of Example 13 was used. No BDA products were evident on the gel, indicating again that a looped adapter is essential for BDA.

Example 18: BDA reaction using the Example-12 adapter ligated to the Example-3 template, and using the 30-base primer of Example 13. No BDA products were evident on the gel, indicating that, like PCR, BDA can sometimes exhibit variable priming.

Example 19: As in Example 18 except that the 21-base primer of Example 13 was used. Several bands of BDA products were seen on the gel, indicating that the BDA reaction occurred with specific priming.

Example 20: BDA reaction using the Example-12 adapter ligated to Arabidopsis DNA digested with Sau3A I; the 30-base primer of Example 13 was also used. Faint bands of various sizes on the gel indicated either that the primers non-specifically bound to the Arabidopsis DNA or that the Arabidopsis DNA contained small sequences substantially homologous to the primers.

Example 21: As in Example 20 except that the 30-base primer of Example 13 was used. No BDA products were evident on the gel, indicating that the Arabidopsis DNA contained no primer target sites for the 30-base primers.

Example 22: BDA reaction of Example-12 adapters ligated together without any intervening template; the 21-base primer of Example 13 was used. A number of bands appeared on the gel, indicating that the primers non-specifically bound to one or more locations on the adapters.

Example 23: As in Example 22 except that the 30-base primer of Example 13 was used. A number of bands having different sizes than the fragments seen in Example 22 appeared on the gel. Again, this indicates that the 30-base primer non-specifically bound to one or more locations on the adapters.

EXAMPLES 24–29

In an effort to better understand the results in Examples 14–23, the reactants in each of the Example 14–23 reactions were individually electrophoresed in a 5% acrylamide gel. The object was to ascertain whether or not ligation had occurred prior to actually beginning BDA.

The following results were obtained as visualized on the gel:

Example 24: Corresponding to Example 15; a single band appeared on the gel which corresponded to the unligated Adapter molecules.

Example 25: A control containing the Example-12 Adapters ligated together; a single band appeared on the gel which corresponded to the size of the ligated Adapters.

Example 26: Corresponding to Examples 22 and 23; a single band was seen on the gel as in Example 25.

Example 27: Corresponding to Examples 20 and 21; a single band was seen on the gel as in Example 25.

Example 28: Corresponding to Examples 18 and 19; a single band was on the gel as in Example 25.

Example 29: Corresponding to Examples 16 and 17; no discrete bands were visible on the gel due to the presence of a multitude of differently sized fragments. This was as expected because Sau3A I-cut duplex Arabidopsis DNA generates a large number of differently sized fragments.

Examples 14–29 indicate that BDA is similar to PCR in that non-specific priming can sometimes occur. Nevertheless, priming does appear to result in actual amplification of DNA.

EXAMPLES 30–43

These Examples comprise an evaluation of BDA amplification of the Example-3 template using the Example-12 adapters and either the 30-base or 21-base primer of Example 13. BDA protocols were as described in Examples 14–23.

The following results were obtained, as visualized on a 1% agarose gel:

Example 30: A "negative PCR control" on an Arabidopsis target DNA, performed using a 1.6-kb template from Arabidopsis with corresponding primers, but containing no DNA polymerase. A single diffuse band was seen on the gel corresponding to the size of the primers.

Example 31: A "positive PCR control" on an Arabidopsis target DNA, performed as in Example 30 but including DNA polymerase. A strong band on the gel at 1.6 kb indicated that PCR occurred.

Example 32: A "negative PCR control" on the Example-3 template, performed using the 21-base and 30-base primers of Example 13 but lacking DNA polymerase. No distinct bands were evident on the gel.

Example 33: A "negative BDA control" on a BDA template, performed using the Example-3 template ligated to the Example-12 adapters, and including the 21-base and 30-base primers of Example 13, but no DNA polymerase. No apparent bands were evident on the agarose gel.

Example 34: A "negative BDA control" for the 21-base primer on a BDA template, performed as in Example 33 but including only the 21-base primer of Example 13. No apparent bands were evident on the agarose gel.

Example 35: A "negative BDA control" for the 30-base primer on a BDA template, performed as in Example 33, but including only the 30-base primer of Example 13. No bands were evident on the agarose gel.

Example 36: A PCR reaction on a BDA template involving 2.0 pg of the Example-3 template ligated to Example-12 adapters and the 21-base and 30-base primers of Example 13. The primary product on the agarose gel was a band having an apparent size of about 263 bp, which substantially agrees with the expected PCR product of such a reaction. Subsequent electrophoresis of this product on 5% polyacrylamide exhibited a band of about 239 bp. The difference in apparent size between the different gels is within a reasonable variability expected for a fragment of 241 bp under these conditions.

Example 37: BDA reaction as in Example 36 but employing only the 21-base primers of Example 13. Two bands were seen on the agarose gel at about 378 and 717 bp.

Example 38: BDA reaction as in Example 36 but employing only the 30-base primers of Example 13. Two bands were seen on the agarose gel at about 473 and 666 bp.

Example 39: A "PCR control" reaction using 0.2 pg of the Example-3 template and the 21-base and 30-base primers of Example 13. An extremely faint band was evident on agarose gel at about 241 bp.

Example 40: A "PCR control" reaction as in Example 39 but using tenfold more template DNA (2.0 pg). This reaction produced a more pronounced band at about 241 bp on agarose gel than did Example 39.

Example 41: PCR reaction on the Example-3 template as in Example 36 but using both the 21-base and 30-base primers and one-tenth the amount of template. Only one faint band at about 241 bp on the agarose gel was evident.

Example 42: BDA reaction as in Example 36 but using the 21-base primer and one-tenth the amount of template. No 30-base primers were used. No bands were evident on the agarose gel.

Example 43: BDA reaction as in Example 37 but using the 30-base primer and one-tenth the amount of template. No bands were evident on the agarose gel.

These Examples (30–43) indicate that BDA produces distinct products having molecular sizes that correspond to the particular primer(s) were used.

The products of Examples 30–43 were further characterized using Southern blotting. The bands from the agarose gel were blotted onto nitrocellulose and probed with the 30-base primer of Example 13 labeled on its 5' end with $^{32}$P.

None of the controls (Examples 30–35) produced any labeled bands on the autoradiogram.

The single band on the gel of Example 36 produced a corresponding strongly labeled band on the autoradiogram.

Each of the two bands seen on the gel of Example 37 produced a corresponding strongly labeled band on the autoradiogram. Since none of Examples 30–35 produced a band on the autoradiogram, BDA has apparently amplified the Example-3 template in Example 37. Moreover, since the region that was probed in the Southern blot was internal to the 21-base primer target site on the template, it was concluded that BDA in Example 37 extended the 21-base primer in the correct direction and faithfully copied the template because the BDA products included the 30-base primer target site as well. The 30-base primer target site is 241 bases away from the 21-base primer target site on the template.

Each of the two bands seen on the gel of Example 38 produced a corresponding strongly labeled band on the autoradiogram. Again, since none of Examples 30–35 produced a band on the autoradiogram, BDA has apparently amplified the template in Example 38.

Each of the single bands seen on the gel of Examples 39–41 produced a corresponding radiolabeled band on the autoradiogram.

From these Examples (30–43) it was concluded that:

1. BDA resulted in replication (and, therefore, amplification) of at least portions of the 341-bp template of Example 3. Control reactions (Examples 32–35) containing starting amounts of the Example-3 template (0.2 pg or 2.0 pg) produced either no products or such small amounts of products that were undetectable as either ethidium bromide-stained bands in agarose or by Southern blotting. Only when the template was actually amplified by PCR or BDA were products detectable. BDA reactions utilizing only a single primer directed the synthesis of easily detectable amounts of fragments that contained sequences of the template.

2. It is known that, in order to visualize a DNA band on an ethidium bromide-stained agarose gel, about 15–30 ng of DNA are required. In the above Examples, the amount of DNA loaded onto the gel was about 15% of the total of the BDA reaction. Thus, the total BDA product was at least 100 ng. If 50 percent of the BDA product was due to sequences of the 341-bp Sau3A I fragment, then the magnitude of amplification seen in these experiments was at least 25,000-fold (50 ng product per 2 pg of starting template).

3. Replication from the 21-base primer extended at least 241 bases in the direction of the 30-base primer target site and faithfully copied the template.

Other experiments were performed to further characterize the products of Examples 30–43. The BDA products were purified from any primers present therewith by centrifugation with three 1-mL washes on Centricon 100 filters and subjected to restriction-mapping analysis on a 5% acrylamide gel. The fragment sizes seen on the acrylamide gel were found to correlate with fragment sizes seen on the 1% agarose gel. Actual fragment lengths on both the 1% agarose and 5% acrylamide gels were determined in a conventional way by plotting the inverse logarithm of the molecular weight of length standards (a 1-kb "ladder") against mobility in each gel. Unknown fragment sizes were interpolated from the nearest known-molecular-weight bands comprising the ladder. The unusual panhandle structure of BDA adapters resulted in an unusual electrophoretic mobility for both monomer and dimer (ligated) forms of the adapter. For example, although the adapters used in these Examples were each 224 bases long, they had an apparent mobility corresponding to about 340 bp. Dimeric forms of these adapters appeared to migrate at rates corresponding to a molecular weight of about twice that of the adapter monomers.

EXAMPLES 44–52

Figure 8:
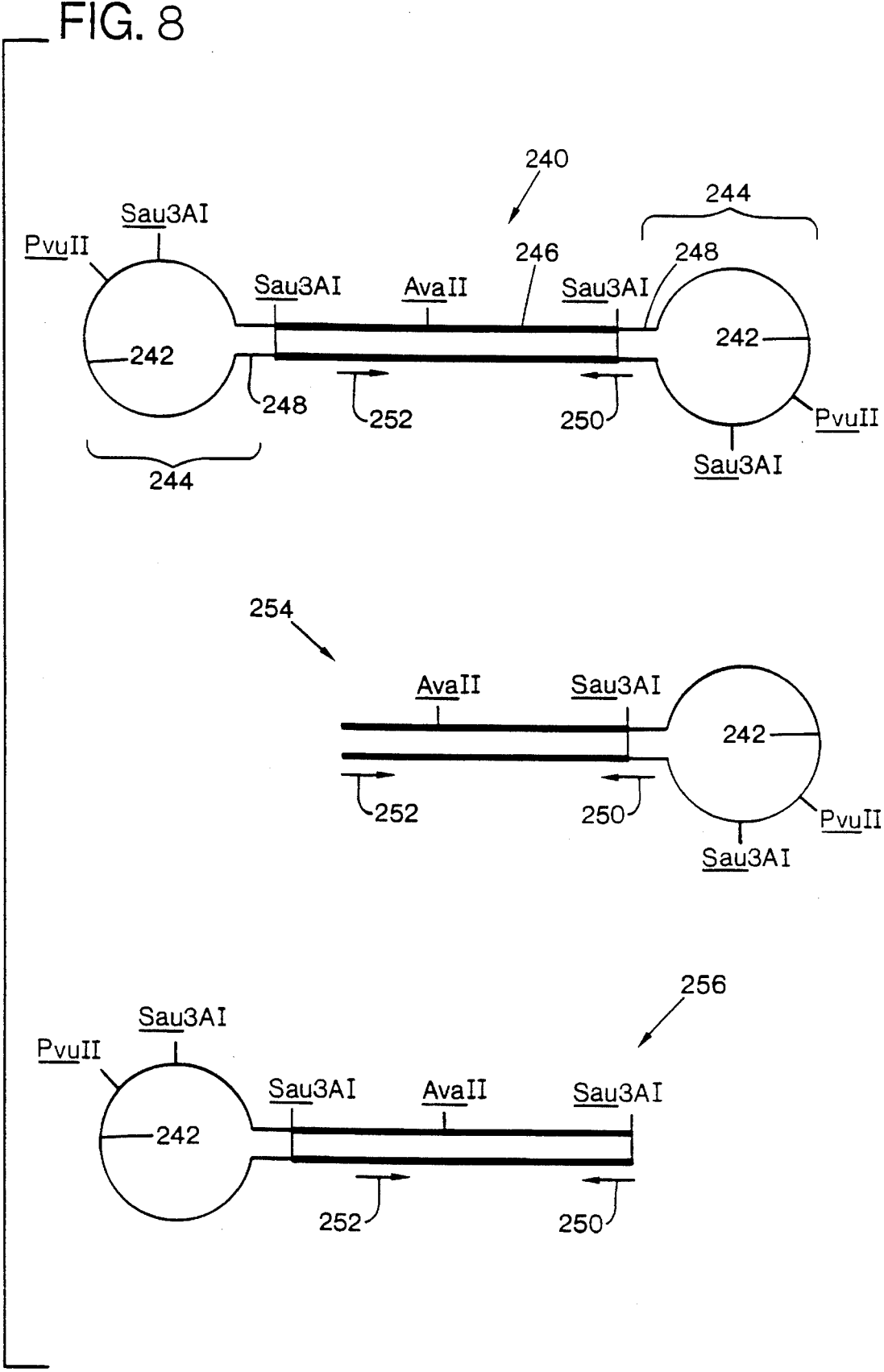
FIG. 8 schematically illustrates BDA products generated from a closed-loop structure comprising a sequence of interest to which BDA adapters have been ligated, with particular emphasis on the location of certain restriction endonuclease cleavage sites useful for ascertaining which BDA products were formed, as detailed in Examples 44–52.

Three restriction endonucleases (PvUII, Sau3A I, and AvaII) were used to further study the BDA products of Examples 37 and 38. Cleavage sites on a closed-loop structure 240 formed by ligating the Example-3 template with the Example-12 adapters are shown in FIG. 8. (Although the maps in FIG. 8 depict, for clarity, the location of the PvuII and Sau3AI recognition sites in the spacer region 242, it will be understood by persons skilled in the art that these enzymes do not efficiently cleave recognition sites unless they are present in duplex DNA.) These restriction endonucleases were selected because each cuts at one or more loci on the closed loop structure 240. A single PvuII site is located in the loop region 242 of the adapter 244. No PvuII sites are located in the template 246. A single AvaII site is present in the template 246, but not in the adapter 244. A Sau3A I site is present where the panhandle region 248 of each adapter 244 is joined to the corresponding end of the template 246 and within the loop 242 of each adapter 244.

The unique AvaII site in the template 246 is 176 bases from the 5'-end of the 21-base primer target site (arrow 250) and 63 bases from the 5'-end of the 30-base primer target site (arrow 252). (These two lengths do not add up exactly to 241 bp because of the locations of the AvaII cutting sites.) The Sau3A sites in the duplex region 248 of the adapter 244 are 341 bp from the 5'-end of the 21-base primer target site 250 and 241 bp from the 5'-end of the 30-base primer target site 252. As shown in FIG. 8, a BDA reaction resulting from priming with a 30-base primer complementary to the 30-base primer target site 252 would be expected to yield the BDA product 254. A BDA reaction resulting from priming with a 21-base primer complementary to the 21-base primer target site 250 would be expected to yield the BDA product 256.

Each Example was prepared as follows, with results as noted:

Example 44: Product from Example 38 cut with Sau3A I.
Example 45: Product from Example 38 cut with PvuII.
Example 46: Product from Example 38 cut with AvaII.
Example 47: Product from Example 38 uncut.
Example 48: Product from Example 37 cut with Sau3A I.
Example 49: Product from Example 37 cut with PvuII.
Example 50: Product from Example 37 cut with AvaII.
Example 51: Product from Example 37 uncut.
Example 52: (PCR control) product from Example 36 uncut.

Results obtained were:

1. Examples 45 and 47 each produced two differently sized bands on a 5% acrylamide gel. The Example-45 bands appeared to be about 712 and 476 bp long, respectively, which is exactly the same size as the two Example-47 bands. Therefore, it was concluded that the two Example-45 bands were apparently not cut by PvuII, indicating either that they lacked the CAGCTG sequence recognized by PvuII or such sequence was present solely in a single-stranded form such as a loop where the enzyme cannot cut. Likewise, Examples 49 and 51 each yielded exactly the same two bands on the gel, having apparent sizes of 712 and 476 bp long, respectively. Therefore, it was concluded that, as in Example 45, the two bands in Example 49 also represented DNA apparently uncuttable by PvuII. Since PvuII-cutting indicates the presence of the loop sequences in double-stranded form, the absence of PvuII cutting in Examples 45 and 49 indicated either the absence of the loop sequences in these Examples or that the loop portion was present only in single-stranded form.

2. The Example 46 reaction exhibited two bands on the gel, having apparent sizes of about 643 and 418 bp, that were smaller than two corresponding bands exhibited by Example 47, one by about 61 bp and the other by about 69 bp. Thus, it was concluded that the two bands in Example 47 each contained an AvaII site, which is unique to the Example-3 template. In addition, Example 46 produced a third very faint band at about 68 bp and the two bands produced in Example 47 were larger than the corresponding bands of Example 46 by about 68 bp. These AvaII-cutting results are consistent with a BDA product structure being linear at one end and terminating at the linear end at the 5' end of the corresponding primer target site. These results are also consistent with BDA amplification of the 341-bp template and are consistent with the 1% agarose analysis and the Southern blotting experiments of Examples 30–43.

3. Example 50 produced a prominent band on the gel sized at about 185 bp. Since the AvaII site is located 176 bp from the 5'-end of the 21-base primer target site, the 185 bp value determined here is well within the margin of error for this type of analysis. Two other substantially fainter but larger bands were seen, but their structure has not yet been determined.

4. Example 44 produced no discernable bands on the gel. In contrast, Example 48 produced a somewhat wide band sized at about 341 bp. This is exactly the size that would be expected for a BDA product primed by the 21-base primer. There does not appear to be sufficient product from Example 44 to ascertain the sizes of any products formed therein.

EXAMPLE 53

This Example illustrates how a representative adapter molecule, as illustrated as item 192 in FIG. 5 and described hereinabove, can be synthesized.

It will be recalled in Example 1 that a plasmid pMIR1 was constructed by ligating the small EcoRI fragment of pIR8 into the unique EcoRI site of a pIB plasmid. The pMIR1 plasmid was transformed into MV1190 cells which were superinfected with M13KO7. Single-stranded pMIR1 DNA was subsequently isolated from the cells, allowed to self-anneal, and cleaved with BamHI. A 224-base adapter was used further in Example 1. However, the BamHI digestion also yielded a larger fragment which contains an *E. coli* replication origin and a gene encoding ampicillin resistance. Cleavage of this single-stranded pMIR1 product with PstI yields a panhandled molecule having a duplex panhandle of about 45–50 bp and a single-stranded loop of about 2.7 kb. The single-stranded loop contains the *E. coli* origin of replication and the ampicillin-resistance gene.

EXAMPLE 54

This Example comprises a test of the ability of BDA to amplify a specific DNA sequence of interest from a mixture of sequences obtained from genomic DNA.

Arabidopsis genomic DNA (0.1 µg; genome size is about 50,000,000 bp) was completely digested with 10 Units of Sau3A I restriction endonuclease. The resulting fragments, having ends sticky for BamHI, were ligated to 0.3 µg of Example-12 adapters to produce looped templates. BDA was performed using a 27-base primer having the following sequence (Seq. ID NO.:9):

5'AAACGACGGCGAGTAATGAACTAAACG3'

This primer was employed because it was known to be effective for identifying individual plaques, plotted on a bacterial "lawn," carrying a portion of the Arabidopsis genome. (Thus, the Arabidopsis genome contains at least one copy of this primer or a sequence homologous to it.) In this Example, it was desired to clone the portion of the Arabidopsis genome containing this sequence or its close homolog.

After a usual number of BDA cycles, examination by gel electrophoresis followed by ethidium bromide staining revealed the presence of two faint bands on the gel. Southern blot analysis using the 27-base primer labeled at the 5' end with $^{32}$P indicated that both bands visible on the gel included a target site for this primer. A control reaction using 0.1 µg of Arabidopsis genomic DNA cut with Sau3A I but not replicated by BDA did not produce any bands detectable on either an ethidium bromide-stained gel or on a Southern blot.

The BDA-amplified genomic DNA was purified on Centricon 100 filters by washing three times with 1 mL distilled water. Approximately one-fourth of the BDA-amplified DNA was then digested using Sau3A I to cleave off the adapters. DNA amplified by BDA was expected to have a first end sticky for BamHI-cut DNA and a second, blunt, end terminating with the primer sequence. Any other DNAs in the mixture (e.g., adapters and genomic fragments not amplified by BDA) were expected to have ends sticky for BamHI-cut DNA only.

The Sau3A I-cut DNA was co-precipitated with 0.1 µg of pUC18 DNA cleaved with HincII and BamHI. Such digestion leaves the pUC18 DNA with a blunt end and an end sticky for BamHI-cut DNA, just like the BDA-amplified DNA. The precipitated DNAs were resuspended in buffer, ligated using T4 ligase overnight at 16° C., and transformed into *E. coli* cells. Selection on plates containing ampicillin yielded 23 colonies.

Restriction analysis of the first seventeen colonies on 1% agarose gels revealed that four colonies contained apparently identically sized inserts (about 300–500 bp). One other colony appeared to contain a rearrangement of pUC18 and the remaining twelve appeared to contain pUC18 without any insert therein.

DNA sequence analysis of the four clones containing identically sized inserts revealed that the inserts in all four had identical sequences. Moreover, each of the inserts yielded DNA fragments having the exact structure of DNA amplified by BDA. Specifically, one end of each fragment was blunt and the other end was sticky for Sau3A I (or BamHI). Sequence analysis from the blunt end of the fragment yielded the following sequence data (Seq. ID NO.:10):

5'AAACGACGGCGAGTAATGAACTAAACGTGTTCTTGTGACGAAGGGCGAG
AGAACTCGCCTTTTTTATTTAAGATAACAGTGCGTGTTGTTGCGTCTTT
TGCAGCATTTCGGAGGTATGACTACCGATAAAGAACTGCCGCAACCTGG3'

Sequence analysis from the sticky end yielded the following sequence data (Seq. ID NO.:11):

5'GATCAGGTAAGTATCATBTCAAGTTTATCTCGTGGTTCTCTGTGTTTAC
TTTTTTGAAGTTCTCAGGCTTCAATGGAAATACTTCTCCCCTTTGAAAT
GTGTGTAGGAGAATAA3'

On each end, the sequence was determined far enough to unambiguously reveal the sequence information sought. The portions of these fragments between the sequenced ends were not determined. Nevertheless, the fragments had the following important features:

(1) The blunt end comprised twenty-seven nucleotides having the exact sequence of the primer. It should be noted that it is possible for a sequence similar but not exactly identical to the primer to be extended in the BDA reaction. However, since the DNA polymerase does not efficiently edit mismatches between the primer and the primer target site, the BDA-amplified DNA will have the exact sequence of the primer, regardless of the downstream sequence. (PCR has the same uncertainty associated with it.) However, as in this Example, production of an amplified DNA product having a blunt end terminating with the primer sequence is a strong indication that the desired SOI was amplified by BDA, since there is virtually no other way for such a product to be produced other than by BDA.

(2) The sequence at the sticky end of the BDA-amplified DNA is exactly as expected of a fragment excised from adapters by cutting with Sau3A I.

Conclusions from this Example were as follows:

(a) BDA will occur when performed using a primer specific for a particular sequence of interest in a genomic DNA such as from Arabidopsis. BDA will generate amplified DNA sequences containing the primer sequence (or a sequence substantially homologous thereto) at a concentration sufficient for detection on ethidium bromide-stained gels. The amplified sequences can be cloned into appropriately cleaved plasmid vectors.

(b) Amplification of DNA on these looped genomic templates resulted from primer binding to primer target sites, as indicated by the binding of labeled primer to specific bands on Southern blots. In addition, the precise alignment of the bands identified in the Southern blots with the ethidium bromide-stained bands on the gels suggests strongly that the ethidium bromide-stained products are the result of BDA specifically initiated by the primer sequence. Sequence analysis of clones derived from the BDA products confirmed the presence of the priming sequence in all cloned fragments.

(b) The BDA products of this Example had structures and sequences that were as predicted for BDA products. At one end, the DNAs were blunt and had a sequence identical to that of the primer. At the other end, the DNA had an end sticky for DNA fragments cut with the same restriction enzyme used to cleave away the adapters. Unamplified DNA molecules or primers would not have blunt first ends and would not terminate on the blunt end with the primer sequence. Since the primer was single-stranded, it was not possible for the DNA ligase to attach the primer fortuitously onto a random DNA fragment. Moreover, there was no evidence of a Sau3A I site at the 3' end of the primer, which is what would be expected for a random fragment (not amplified by BDA) ligated to a single-stranded primer. The only Sau3A I site in the BDA product was at the sticky end thereof.

(d) If these analyses had produced several different clones each with a different DNA sequence, one might conclude that either the priming sequence was present in several copies in the genome (like a repetitive sequence) or the BDA process used to generate them was prone to artifactual amplification of sequences with no relation to the primer. But, the isolation of four identical clones, and no others, containing genomic DNA amplified by BDA suggests strongly that the BDA reaction performed here targeted a single genomic sequence of interest and that part of the sequence of interest was at least homologous to (if not identical to) the primer used in the BDA reaction.

(e) The four identical cloned fragments reported here were apparently produced by a BDA reaction directed by specific priming of a template hybridized to a homologous (or identical) sequence in the Arabidopsis genome.

While the invention has been described in connection with preferred embodiments and numerous examples, it will be understood that it is not limited to these embodiments and examples. On the contrary, it is intended to cover all alternatives, modifications, and equivalents as may be included within the true spirit and scope of the invention as defined by the appended claims.

I claim:

1. A method for amplifying a DNA sequence of interest in a DNA-containing sample, the method comprising:

(a) cleaving the DNA in the sample to form discrete duplex DNA fragments having ligatable ends each including a 3' terminus and a 5' terminus, wherein at least one of the duplex DNA fragments comprises a sequence of interest and a primer target site ligated to the sequence of interest with or without intervening sequences;

(b) ligating the duplex DNA fragments produced in step (a) to adapter polynucleotides to form ligated duplexes, the adapter polynucleotides each having a structure as shown schematically in FIG. 2A or FIG. 2B and comprising a first sequence 51 in FIG. 2A (or 51a or 51b in FIG. 2B); a second sequence 52 in FIG. 2A for 52a or 52b in FIG. 2B) complementary to the first sequence; a spacer sequence situated between the first sequence and second sequence, the spacer sequence permitting the first sequence and the second sequence on any of said adapter polynucleotides to form a duplex of each other with the spacer sequence forming a single-stranded loop connecting the first sequence and second sequence together; and at least one adapter end region comprising a duplex of the first sequence and the second sequence, the adapter end region having a 3' terminus and a 5' terminus and being ligatable to the ends of the duplex DNA fragments such that, in each ligation, at least one of the 3' and 5' termini of an adapter polynucleotide becomes ligated to the corresponding 5' or 3' terminus, respectively, of an end of a duplex DNA fragment;

(c) denaturing the ligated duplexes formed in step (b) to form templates;

(d) annealing oligonucleotide primers to the templates, each primer being homologous with the primer target site so as to anneal to a primer target site under conditions in which a primer and a primer target site can anneal to each other and form a duplex of each other at which primer extension can occur; and (e) extending the annealed primers under DNA replication conditions to form duplex products, the duplex products comprising the template and a segment homologous with the template, the homologous segment being capable of forming a duplex with itself and representing an amplification of the sequence of interest.

2. A method as recited in claim 1 wherein step (a) comprises cleaving the DNA in the sample using a restriction endonuclease.

3. A method as recited in claim 2 wherein step (a) produces duplex DNA fragments having ligatable ends that are sticky.

4. A method as recited in claim 3 wherein step (b) comprises ligating the duplex fragments to adapter polynucleotides each having an adapter end region sticky for a sticky end of a duplex DNA fragment produced in step (a).

5. A method as recited in claim 1 wherein step (e) is performed using all four dNTPs and a DNA polymerizing agent.

6. A method as recited in claim 5 wherein the DNA polymerizing agent is a DNA polymerase.

7. A method as recited in claim 6 wherein the DNA polymerase is thermostable to DNA denaturing temperatures.

8. A method as recited in claim 1 wherein step (b) is performed using a DNA ligase.

9. A method as recited in claim 1 wherein, in step (e), said DNA replication conditions include the presence of a DNA polymerase and incubation at a temperature conducive for the DNA polymerase to add nucleotides to the primer.

10. A method as recited in claim 1 further comprising, after step (e), the steps:

(f) incubating the duplex products formed in step (e) under denaturing conditions to form denatured products;

(g) annealing oligonucleotide primers to the denatured products, each primer being homologous with the primer target site on a denatured product so as to anneal to a primer target site under conditions in which the primers and the primer target sites anneal to each other and form duplexes of each other at which primer extension can occur; and (h) extending the annealed primers under DNA replication conditions to form more of the duplex products.

11. A method as recited in claim 10 wherein steps (f)–(h) are repeated at least once.

12. A method as recited in claim 1 wherein, in the duplex products formed in step (e), the segment homologous to the template comprises the primer and sequences complementary to the first sequence, the second sequence, the spacer sequence, and at least a portion of the sequence of interest.

13. A method for amplifying a DNA sequence of interest in a DNA-containing sample, the method comprising:

(a) cleaving the DNA in the sample to form discrete duplex DNA fragments having ligatable ends, wherein at least one of said fragments comprises a sequence of interest and a primer target site ligated to the sequence of interest with or without intervening sequences;

(b) ligating the duplex fragments produced in step (a) to adapter polynucleotides to form ligated duplexes, each adapter polynucleotide having a structure as schematically shown FIG. 2A and comprising a first single-stranded sequence, a second single-stranded sequence complementary to the first single-stranded sequence, a spacer sequence situated between the first and second single-stranded sequences, and at left one end comprising a duplex of the first single-stranded sequence and the second single-stranded sequence, the duplex having a 3' terminus and a 5' terminus and being ligatable to the ends of the duplex fragments such that at least one of the 3' and 5' termini of the adapters becomes ligated to the corresponding 5' or 3' end, respectively, of the duplex fragments;

(c) denaturing the ligated duplexes formed in step (b) to form templates;

(d) annealing oligonucleotide primers to the templates each primer being homologous with the primer target site so as to anneal to a primer target site under conditions in which a primer and a primer target site can anneal to each other and form a duplex of each other at which primer extension can occur; and (e) extending the annealed primers under DNA replication conditions to form duplex products, the duplex products comprising the template and a segment homologous with the template, the homologous segment being capable of forming a duplex with itself and representing an amplification of the sequence of interest.

14. A method as recited in claim 13 wherein each adapter comprises a duplex panhandle formed by base-pairing of the first and second self-complementary sequences.

15. A method as recited in claim 14 wherein the duplex panhandle comprises a polylinker.

16. A method for amplifying a DNA sequence of interest in a DNA-containing sample, the method comprising:

(a) cleaving the DNA in the sample to form discrete duplex DNA fragments having ligatable ends, wherein at least one of said fragments comprises a sequence of interest and a primer target site ligated to the sequence of interest with or without intervening sequences;

(b) ligating the duplex fragments produced in step (a) to adapter polynucleotides to form ligated duplexes, each adapter polynucleotide having a structure as schematically shown FIG. 2B and comprising a first single-stranded sequence, a second single-stranded sequence complementary to the first single-stranded sequence, a spacer sequence situated between the first and second single-stranded sequences, and at ,least one end comprising a duplex of the first single-stranded sequence and the second single-stranded sequence, the duplex having a 3' terminus and a 5' terminus and being ligatable to the ends of the duplex fragments such that at least one of the 3' and 5' termini of the adapters becomes ligated to the corresponding 5' or 3' end, respectively, of the duplex fragments;

(c) denaturing the ligated duplexes formed in step (b) to form templates;

(d) annealing oligonucleotide primers to the templates each primer being homologous with the primer target site so as to anneal to a primer target site under conditions in which a primer and a primer target site can anneal to each other and form a duplex of each other at which primer extension can occur; and (e) extending the annealed primers under DNA replication conditions to form duplex products, the duplex products comprising the template and a segment homologous with the template, the homologous segment being capable of forming a duplex with itself and representing an amplification of the sequence of interest.

17. A method as recited in claim 16 including the step, before step (b), of chemically altering the adapters so as to make the ends thereof ligatable to the duplex DNA fragments but not to each other.

18. A method as recited in claim 17 wherein the adapters are chemically altered by removing a 5' phosphate on each ligatable end thereof.

19. A method for increasing the number of copies of a nucleic acid sequence of interest in a DNA-containing sample, comprising:

(a) providing adapter polynucleotides having a structure as shown schematically in FIG. 2A or FIG. 2B, the adapter polynucleotides comprising a first sequence 51 in FIG. 2A (or 51a or 51b in FIG. 2B); a second sequence 52 in FIG. 2A (or 52a or 52b in FIG. 2B) complementary to the first sequence; a spacer sequence situated between the first sequence and the second sequence, the spacer sequence permitting the first sequence and second sequence on any of said adapter polynucleotides to form a duplex of each other with the spacer sequence forming a single-stranded loop connecting the first sequence and second sequence together; and at least one end comprising a duplex of the first sequence and the second sequence, the duplex having a 3' terminus and a 5' terminus;

(b) cleaving the DNA in the sample into linear duplex DNA fragments having ligatable ends each including a 3' terminus and a 5' terminus, wherein at least one of said duplex DNA fragments contains a sequence of interest and a primer target site ligated to the sequence of interest with or without intervening sequences;

(c) ligating the adapter polynucleotides provided in step (a) to the duplex DNA fragments formed in step (b) to form ligated duplexes, wherein, in each ligation, at least one of said 3' and 5' termini of an adapter polynucleotide becomes ligated to a 5' or 3' terminus, respectively, of a duplex DNA fragment;

(d) denaturing the ligated duplexes formed in step (c) to form templates;

(e) annealing DNA oligonucleotide primers to the templates formed in step (d), each primer being homologous with the primer target site so as to anneal to a primer target site under conditions in which a primer and a primer target site can anneal to each other and form a duplex of each other at which primer extension can occur; and (f) extending the annealed primers under DNA replication conditions to form duplex products, the duplex products comprising the template and a segment homologous with the template, the homologous segment being capable of forming a duplex with itself and representing an increase in the number of copies of the sequence of interest.

20. A method as recited in claim 19 including, after step (f), the steps:

(g) denaturing the duplex products formed in step (f) to form denatured products;

(h) annealing oligonucleotide primers to the denatured products, each primer being homologous with the primer target site on a denatured product so as to anneal to a primer target site under conditions in which the primers and primer target site anneal to each other and form duplexes of each other at which primer extension can occur; and (i) extending the annealed primers under DNA replication conditions to form more of the duplex products.

21. A method as recited in claim 19 including the step, before step (f), of adding dNTPs and a DNA polymerizing agent to the ligated duplexes.

22. A method as recited in claim 21 wherein at least one of said dNTPs is labeled.

23. A method as recited in claim 20 wherein steps (g)–(i) are repeated at least once.

24. A method for increasing the number of copies of a nucleic acid sequence of interest in a DNA-containing sample, comprising:

(a) providing adapter polynucleotides as shown schematically in FIG. 2A, the adapter polynucleotides comprising a first single-stranded sequence, a second single-stranded sequence complementary to the first single-stranded sequence, a spacer sequence situated between the first and second single-stranded sequences, and at least one end comprising a duplex of the first single-stranded sequence and the second single-stranded sequence, the duplex having a 3' terminus and a 5' terminus;

(b) cleaving the DNA in the sample into linear duplex DNA fragments having ends ligatable to the ligatable ends of the adapters, wherein at least one of said fragments contains a sequence of interest and a primer target site ligated to the sequence of interest with or without intervening sequences;

(c) ligating the adapter polynucleotides provided in step (a) to the fragments formed in step (b) to form ligated duplexes, wherein, in each ligation, at least one of said 3' and 5' termini of the adapter becomes ligated to a 5' or 3' terminus, respectively, of a fragment;

(d) denaturing the ligated duplexes formed in step (c) to form templates;

(e) annealing DNA oligonucleotide primers to the templates formed in step (d), each primer being homologous with the primer target site so as to anneal to a primer target site under conditions in which a primer and a primer target site can anneal to each other and form a duplex of each other at which primer extension can occur; and (f) extending the annealed primers under DNA replication conditions to form duplex products, the duplex products comprising the template and a segment homologous with the template, the homologous segment being capable of forming a duplex with itself and representing an increase in the number of copies of the sequence of interest.

25. A method as recited in claim 24 wherein the adapters include a panhandle duplex of the first and second single-stranded sequences, wherein the ligatable end of the adapter is situated on a first end of the panhandle duplex and the spacer forms a single-stranded loop on an opposing second end of the panhandle duplex.

26. A method as recited in claim 25 wherein the panhandle duplex includes at least one restriction-enzyme cleavage site.

27. A method as recited in claim 25 wherein the panhandle duplex has a length of at least about 15 base pairs.

28. A method as recited in claim 25 wherein the spacer comprises at least about ten nucleotides.

29. A method for increasing the number of copies of a nucleic acid sequence of interest in a DNA-containing sample, comprising:

(a) providing adapter polynucleotides as shown schematically in FIG. 2B, the adapter polynucleotides comprising a first single-stranded sequence, a second single-stranded sequence complementary to the first single-stranded sequence, a spacer sequence situated between the first and second single-stranded sequences, and at least one end comprising a duplex of the first single-stranded sequence and the second single-stranded sequence, the duplex having a 3' terminus and a 5' terminus;

(b) cleaving the DNA in the sample into linear duplex DNA fragments having ends ligatable to the ligatable ends of the adapters, wherein at least one of said fragments contains a sequence of interest and a primer target site ligated to the sequence of interest with or without intervening sequences;

(c) ligating the adapter polynucleotides provided in step (a) to the fragments formed in step (b) to form ligated duplexes, wherein, in each ligation, at least one of said 3' and 5' termini of the adapter becomes ligated to a 5' or 3' terminus, respectively, of a fragment;

(d) denaturing the ligated duplexes formed in step (c) to form templates;

(e) annealing DNA oligonucleotide primers to the templates formed in step (d), each primer being homologous with the primer target site so as to anneal to a primer target site under conditions in which a primer and a primer target site can anneal to each other and form a duplex of each other at which primer extension can occur; and (f) extending the annealed primers under DNA replication conditions to form duplex products, the duplex products comprising the template and a segment homologous with the template, the homologous segment being capable of forming a duplex with itself and representing an increase in the number of copies of the sequence of interest.

30. A method as recited in claim 29 wherein each adapter comprises a first strand that includes the first and second single-stranded sequences and the spacer, and a second strand that includes sequences complementary to the spacer and the first and second single-stranded sequences.

31. A method for increasing the number of copies of a nucleic acid sequence of interest in a DNA-containing sample, comprising:

(a) providing adapter polynucleotides having a structure as shown schematically in FIG. 2A or FIG. 2B, the adapter polynucleotides comprising a first sequence 51 in FIG. 2A (or 51a or 51b in FIG. 2B); a second sequence 52 in FIG. 2A (or 52a or 52b in FIG. 3B); a spacer sequence situated between the first sequence and the second sequence, the spacer sequence permitting the first sequence and the second sequence on any of said adapter polynucleotides to form a duplex of each other with the spacer sequence forming single-stranded loop connecting the first sequence and the second sequence together; and at least one adapter end region comprising a duplex of the first sequence and the second sequence, the adapter end region having a 3' terminus and a 5' terminus;

(b) cleaving the DNA in the sample into linear duplex DNA fragments having ligatable ends each including a 3' terminus and a 5' terminus, wherein at least one of said duplex DNA fragments contains a sequence of interest and a primer target site ligated to the sequence of interest with or without intervening sequences;

(c) ligating the adapter polynucleotides provided in step (a) to the duplex DNA fragments formed in step (b) to form ligated duplexes, wherein, in each ligation, at least one of said 3' and 5' termini of an adapter polynucleotide becomes ligated to a 5' or 3' terminus, respectively, of a duplex DNA fragment;

(d) providing single-stranded oligonucleotide primers complementary to the primer target site;

(e) adding dNTPs, a DNA polymerization agent, and the primers to the ligated duplexes;

(f) annealing the primers to the primer target sites under conditions in which a primer and a primer target site can anneal to each other and form a duplex of each other at which primer extension can occur; and (g) extending the annealed primers under DNA replication conditions to form duplex products, the duplex products comprising the template and a segment homologous with the template, the homologous segment being capable of forming a duplex with itself and representing an increase in the number of copies of the sequence of interest.

32. A method as recited in claim 31 further comprising the step, after step (e) but before step (f), of denaturing the ligated duplexes.

33. A method as recited in claim 31 wherein step (d) comprises providing primers having a length of at least about 15 bases.

34. A method as recited in claim 31 further comprising the step, before step (c), of adding an amount of adapters to the fragments representing a molar excess of adapters relative to fragments.

35. A method as recited in claim 31 wherein step (e) comprises adding an amount of primers representing a molar excess relative to the ligated duplexes.

36. A method for amplifying a DNA sequence of interest in a DNA-containing sample, the method comprising:

(a) providing DNA adapters having a structure as shown schematically in FIG. 2A or FIG. 2B, the adapters comprising a first sequence 51 in FIG. 2A (or 51a or 51b in FIG. 2B) and a second sequence 52 in FIG. 2A (or 52a or 52b in FIG. 2B) complementary to the first sequence, each said first sequence and second sequence having a length of at least about 15 bases; a spacer sequence situated between the first sequence and the second sequence and having a length of at least about ten bases; and at least one adapter end region comprising a duplex of the first sequence and the second sequence, the adapter end region having a sticky 5' or 3' terminus;

(b) cleaving the DNA in the sample into discrete linear duplex DNA fragments having sticky 3' or 5' termini compatible with the sticky 5' or 3' termini, respectively, of the adapters, wherein at least one of said duplex DNA fragments comprises a primer target site of at least about 15 bases, and a sequence of interest located adjacent the primer target site;

(c) ligating the adapters provided in step (a) to the duplex DNA fragments formed in step (b) under ligating conditions to form ligated duplexes, wherein, in each ligation, at least one of said 3' and 5' termini of the adapter becomes ligated to a 5' or 3' terminus, respectively, of a fragment;

(d) providing single-stranded oligonucleotide primers complementary to the primer target site and having a length of at least about 15 bases;

(e) adding dNTPs, a DNA polymerase, and the primers to the ligated duplexes;

(f) denaturing the ligated duplexes to form templates;

(g) annealing the primers to the primer target sites on the templates;

(h) extending the annealed primers under DNA replication conditions to form duplex products, the duplex products comprising a first region containing the primer annealed to the primer target site, and a second region adjacent the first region, the second region comprising the spacer region and the sequence of interest;

(i) incubating the duplex products under denaturing conditions to form denatured products;

(j) annealing oligonucleotide primers to the denatured products, each primer being homologous with the primer target site so as to anneal to a primer target site on a denatured product under conditions in which a primer and a primer target site can anneal to each other and form a duplex of each other at which primer extension can occur;

(k) extending the annealed primers under DNA replication conditions to form more of the duplex products; and (l) repeating steps (i)–(k) a sufficient number of times until a desired amount of the sequence of interest is obtained.

37. A method as recited in claim 36 wherein step (b) is performed using a restriction endonuclease.

38. A method as recited in claim 36 wherein step (c) is performed using a DNA ligase.

39. A method as recited in claim 36 wherein step (f) comprises heat-denaturing the ligated duplexes.

40. A method as recited in claim 39 wherein the heat-denaturing is performed by heating to about 95° C.

41. A method as recited in claim 39 wherein step (g) is performed at a temperature within a range of about 50° C. to about 70° C.

42. A method for amplifying a DNA sequence of interest in a DNA-containing sample, the method comprising:

(a) providing DNA adapters as shown schematically in FIG. 2A, the DNA adapters comprising a first single-stranded sequence and a second single-stranded sequence complementary to the first single-stranded sequence, each said first and second single-stranded sequences having a length of at least about 15 bases, a spacer sequence situated between the first and second single-stranded sequences and having a length of at least about ten bases, and at least one end comprising a duplex of the first single-stranded sequence and the second single-stranded sequence, the end having a sticky 5' or 3' terminus;

(b) cleaving the DNA in the sample into linear duplex DNA fragments having sticky termini compatible with the sticky termini of the adapters, wherein at least one of said duplex fragments comprises a primer target site of at least about 15 bases, and a duplex sequence of interest adjacent the primer target site;

(c) ligating the adapters provided in step (a) to the fragments formed in step (b) under ligating conditions to form ligated duplexes, wherein, in each ligation, at least one of said 3' and 5' termini of the adapter becomes ligated to a 5' or 3' terminus, respectively, of a fragment;

(d) providing single-stranded oligonucleotide primers complementary to the primer target site and having a length of at least about 15 bases;

(e) adding dNTPs, a DNA polymerase, and the primers to the ligated duplexes;

(f) denaturing the ligated duplexes to form templates;

(g) annealing the primers to the primer target sites on the templates;

(h) extending the annealed primers under DNA replication conditions to form duplex products, the duplex products comprising a first duplex region containing the primer annealed to the primer target site, and a second duplex region adjacent the first duplex region, the second duplex region comprising the spacer region and the sequence of interest;

(i) incubating the duplex products under denaturing conditions to form denatured products;

(j) annealing oligonucleotide primers to the denatured products, each primer being homologous with the primer target site so as to anneal to a primer target site on a denatured product under conditions in which a primer and a primer target site can anneal to each other and form a duplex of each other at which primer extension can occur;

(k) extending the annealed primers under DNA replication conditions to form more of the duplex products; and (l) repeating steps (i)–(k) a sufficient number of times until a desired amount of the sequence of interest is obtained.

43. A method as recited in claim 36 wherein step (h) comprises extending the annealed primers to form duplex products each comprising the template and a segment complementary to the template that includes the primer and the primer target site, as well as sequences complementary to the first sequence, the second sequence, the spacer, and the sequence of interest.

44. A method as recited in claim 36 wherein step (l) is repeated about n times, wherein n=30 to 60.

* * * * *

UNITED STATES PATENT AND TRADEMARK OFFICE
CERTIFICATE OF CORRECTION

PATENT NO. : 5,470,724
DATED : November 28, 1995
INVENTOR(S) : Kevin G. Ahern It is certified that error appears in the above-identified patent and that said Letters Patent is hereby corrected as shown below:

In the Specification:

Column 17, lines 23-24, "Yanisch-Perron et al., Gene 33:103[14] 119 (1985)" should be --Yanisch-Perron et al., Gene 33:103-119 (1985)--.

Column 19, lines 23-29, Seq. ID No. 3, and page 36, lines 1-4), replace the sequence with the following sequence:

-- 5'gatctgtctatttcgttcatccatagttgcctgactccccgtcgtgtaga
taactacgatacgggagggcttaccatctggccccagtgctgcaatgata
ccgcgagacccacgctcaccggctccagatttatcagcaataaaccagcc
agccggaagggccgagcgcagaagtggtcctgcaactttatccgcctcca
tccagtctattaattgttgccgggaagctagagtaagtagttcgccagtt
aatagtttgcgcaacgttgttgccattgctacaggcatcgtggtgtcacg
ctcgtcgtttggtatggcttcattcagctccggttcccaac$^{3'}$ --

Column 22, replace the sequence labelled "267-base EcoRI-cut Adapter:" with the following:

-- 267-base EcoRI-cut Adapter:
5'GAATTCGAGCTCGGTACCCGGGGATCCTCTAGAGTCGACCTGCA
GGCATGCAAGCTcgccattcgccattcaggctgcgcaactgttgggaagggcgatcggtgcggg
cctcttcgctattacgccagctggcgaaaggggatgtgctgcaaggcgattaagttgggtaacgccagggtt
ttcccagtcacgacgttgtaaaacgacggccagtaAGCTTGCATGCCTGCAGGTCGTC
TCTAGAGGATCCCCGGGTACCGAGCTCG$^{3'}$ --

UNITED STATES PATENT AND TRADEMARK OFFICE
CERTIFICATE OF CORRECTION

PATENT NO. : 5,470,724
DATED : November 28, 1995
INVENTOR(S) : Kevin G. Ahern

It is certified that error appears in the above-identified patent and that said Letters Patent is hereby corrected as shown below:

Columns 29-30, lines 43-45, Seq. ID No. 11, replace the sequence with the following sequence:

-- 5'GATCAGGTAAGTATCATCTCAAGTTTATCTCGTGGTTCTC
TGTGTTTACTTTTTTGAAGTTCTCAGGCTTCAATGGAAATACTTC
TCCCCTTTGAAATGTGTGTAGGAGAATAA3' --

In the Claims:
Column 43, line 26, "left" should be --least--.

Column 47, line 4, "FIG. 3B" should be --FIG. 2B--.

Signed and Sealed this

Twenty-first Day of October 1997

Attest:

BRUCE LEHMAN

Attesting Officer

Commissioner of Patents and Trademarks